(12) United States Patent
Najarian et al.

(10) Patent No.: US 10,610,113 B2
(45) Date of Patent: Apr. 7, 2020

(54) MINIATURE PIEZOELECTRIC CARDIOVASCULAR MONITORING SYSTEM

(71) Applicant: THE REGENTS OF THE UNIVERSITY OF MICHIGAN, Ann Arbor, MI (US)

(72) Inventors: Kayvan Najarian, Northville, MI (US); Kenn Oldham, Ann Arbor, MI (US); Daniel Slavin, Ann Arbor, MI (US); Ashwin Belle, Ann Arbor, MI (US); Kevin R. Ward, Superior Township, MI (US); Sardar Ansari, Richmond, VA (US); Rodney C. Daniels, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 582 days.

(21) Appl. No.: 14/675,062

(22) Filed: Mar. 31, 2015

(65) Prior Publication Data

US 2015/0305632 A1 Oct. 29, 2015

Related U.S. Application Data

(60) Provisional application No. 61/972,750, filed on Mar. 31, 2014.

(51) Int. Cl.
*A61B 5/00* (2006.01)
*A61B 5/0295* (2006.01)
(Continued)

(52) U.S. Cl.
CPC .......... *A61B 5/0295* (2013.01); *A61B 5/6802* (2013.01); *A61B 5/6831* (2013.01);
(Continued)

(58) Field of Classification Search
CPC ... A61B 5/021; A61B 5/02055; A61B 5/0295; G06F 19/3418
See application file for complete search history.

(56) References Cited

U.S. PATENT DOCUMENTS 5,807,267 A 9/1998 Bryars et al.
6,491,647 B1 * 12/2002 Bridger .................. A61B 5/021
128/900

(Continued)

FOREIGN PATENT DOCUMENTS

WO WO-2011/051819 A1 5/2011

OTHER PUBLICATIONS

Abhinav et al., Nadi Yantra: a robust system design to capture the signals from the radial artery for assessment of the autonomic nervous system non-invasively, J. Biomed. Sci. and Engineer., 2(7):471-9 (2009).

(Continued)

*Primary Examiner* — Michael J D Abreu
(74) *Attorney, Agent, or Firm* — Marshall, Gerstein & Borun LLP

(57) ABSTRACT

The invention is a passive, wearable sensor that uses a thin piezoelectric material to produce a time history of blood pressure of the patient, with signal processing algorithms to extract physiological information. The sensor consists of a piezoelectric transducer set in a polymer laminate that can be applied to the finger or wrist of the patient. During use, a combination of compressive and bending deformation in the piezoelectric layer in response to blood pressure in the finger or wrist as a voltage output. Using signal processing techniques, the raw signal is filtered and decomposed to obtain a information to form derivative signals such as blood pressure, pulse pressure, pulse pressure variability, heart rate, heart rate variability, and respiratory rate which can be (Continued)

very important pre-cursors in the monitoring of the patient's physiological conditions.

24 Claims, 20 Drawing Sheets

(51) Int. Cl.
  *A61M 5/172* (2006.01)
  *A61B 5/024* (2006.01)
  *A61B 5/02* (2006.01)
  *A61B 5/11* (2006.01)

(52) U.S. Cl.
  CPC .......... *A61B 5/7207* (2013.01); *A61B 5/7235* (2013.01); *A61M 5/1723* (2013.01); *A61B 5/02007* (2013.01); *A61B 5/02438* (2013.01); *A61B 5/11* (2013.01); *A61B 2562/0261* (2013.01); *A61B 2562/06* (2013.01)

(56) References Cited

U.S. PATENT DOCUMENTS

| | | | |
|---|---|---|---|
| 6,916,289 | B2 | 7/2005 | Schnall |
| 6,939,304 | B2 | 9/2005 | Schnall et al. |
| 7,374,540 | B2 | 5/2008 | Schnall |
| 7,621,877 | B2 | 11/2009 | Schnall |
| 7,806,831 | B2 | 10/2010 | Lavie et al. |
| 7,819,811 | B2 | 10/2010 | Schnall |
| 8,160,703 | B2 | 4/2012 | Stickney et al. |
| 8,485,448 | B2 | 7/2013 | Maizlin et al. |
| 8,615,290 | B2 | 12/2013 | Lin et al. |
| 2003/0135124 | A1* | 7/2003 | Russell ............... A61B 5/02007 600/500 |
| 2006/0079773 | A1* | 4/2006 | Mourad ................ A61B 5/031 600/438 |
| 2007/0287923 | A1 | 12/2007 | Adkins et al. |
| 2008/0214903 | A1* | 9/2008 | Orbach ................ G06Q 50/22 600/301 |
| 2010/0130874 | A1 | 5/2010 | Joeken |
| 2011/0028801 | A1 | 2/2011 | Koh |
| 2011/0166461 | A1 | 7/2011 | Susstrunk et al. |
| 2012/0065526 | A9 | 3/2012 | Kopetsch et al. |
| 2012/0095352 | A1 | 4/2012 | Tran |
| 2012/0259179 | A1 | 10/2012 | Sullivan et al. |
| 2013/0281795 | A1 | 10/2013 | Varadan |
| 2014/0039330 | A1* | 2/2014 | Seo ...................... A61B 5/0452 600/509 |
| 2014/0174189 | A1 | 6/2014 | Pan et al. |

OTHER PUBLICATIONS

Almeida et al., Machine Learning Techniques for Arterial Pressure Waveform Analysis, J. Pers. Med., 3(2):82-101 (2013).
Ansari et al., Extraction of respiratory rate from impedance signal measured on arm: A portable respiratory rate measurement device, IEEE Conference on Bioinformatics and Biomedicine (IEEE BIBM 2009), pp. 197-202 (Nov. 2009).
Ansari et al., Impedance plethysmography on the arms: Respiration monitoring, The First Workshop on Knowledge Engineering, Discovery and Dissemination in Heatlh, The 2010 IEEE International Conference on Bioinformatics & Biomedicine (BIBM2010), Hong Kong (Dec. 18-21, 2010).
Arpaia et al., A real-time non-invasive system monitoring haemodynamic parameters in critical conditions by peripheral blood pressure wave analysis, The Technical Committee 4 of IMEKO: International Measurement Confederation (2007).
Belova et al., Wavelet transform: A better approach for the evaluation of instantaneous changes in the heart rate variability, Autonomic Neuroscience: Basic and Clinical, 131:107-22 (2007).
Borges Ferreira, Assessment of haemodynamic parameters—New approach to piezoelectric sensors, Dissertação de Mestrado em Engenharia Biomédica, Departamento De Física, Universidade de Coimbra (Sep. 2008).
Bsoul et al., Abstract P115: Prediction of severity of blood volume loss using features based on P,T, and QRS waves, Circulation, Proceedings of, Best Original Resuscitation Science, Moderated Poster Session, 120:S1466 (2009).
Chiu et al., Development of a piezoelectric polyvinylidene fluoride (PVDF) polymer-based sensor patch for simultaneous heartbeat and respiration monitoring, Sensors and Actuators A, 189:328-34 (2013).
Clemente et al., A piezo-film-based measurement system for global haemodynamic assessment, Physiol. Meas., 31(5):697-714 (2010).
Digiglio et al., Microflotronic arterial tonometry for continuous wearable non-invasive hemodynamic monitoring, Ann. Biomedical Engineer., 42(11):2278-88 (2014).
Gong et al., A wearable and highly sensitive pressure sensor with ultrathin gold nanowires, Nature Communications (Feb. 4, 2014).
Ji et al., Abstract 2: Prediction of Hypovolemia Severity Using ECG Signal with Wavelet Transformation Analysis From a Mobile Armband, Circulation, Best of the Best Oral Abstract Presentations, 120:S1441 (2009).
Ji et al., Abstract P195: Incorporating physiological signals to blood loss prediction based on discrete wavelet transformation, Circulation, Best Original Resuscitation Science, Moderated Poster Session, 120:S1483 (2009).
Ji et al., Heart rate variability analysis during central hypovolemia using wavelet transformation, J. Clin. Monit. Comput., 27(3):289-302 (2013).
Kalange et al., Piezoelectric sensor for human pulse detection, Defence Sci., 57(1):109-14 (2007).
Kumar et al., Design and implementation of a Bluetooth-based band-aid pulse rate sensor, Proc. of SPIE, vol. 7980 (2011).
Lang et al., Review of some lesser-known applications of piezoelectric and pyroelectric polymers, Appl. Phys. A, 85:125-34 (2006).
Li et al., Flexible, transparent, pressure-sensitive microfluidic array for artificial tactile applications, pp. 441-442, Solid State Sensors, Actuators and Microsystems Workshop, Hilton Head Island, South Carolina (Jun. 8-12, 2014).
McGrath et al., Pulse oximeter plethysmographic waveform changes in awake, spontaneously breathing, hypovolemic volunteers, Anesthesia Analgesia, 112(2):369-74 (2011).
McLaughlin et al., Piezoelectric sensor determination of arterial pulse wave velocity, Physiol. Meas., 24(3):693-702 (2003).
Nie et al., A microdroplet-based capacitive sensing matrix for tactile applications, Solid-State Sensors, Actuators and Microsystems Workshop, Hilton Head Island, South Carolina (Jun. 8-12, 2014).
Scully et al., Using time-frequency analysis of the photoplethysmographic waveform to detect the withdrawal of 900 mL blood, Society for Technology in Anesthesia, 115(1):74-81 (2012).
Stein et al., Insights from the study of heart rate variability, Ann. Rev. Med., 50:249-61 (1999).
Ward et al., Abstract P191: Use of low level physiologic signals and machine learning to derive important homodynamic variables during acute volume loss, Circulation, Best Original Resuscitation Science, Moderated Poster Session, 120:S1482-3 (2009).
International Search Report and Written Opinion, International Application No. PCT/US2015/023533, dated Jul. 9, 2015.
International Preliminary Report on Patentability for Application No. PCT/US2015/023533 dated Oct. 4, 2016.

* cited by examiner

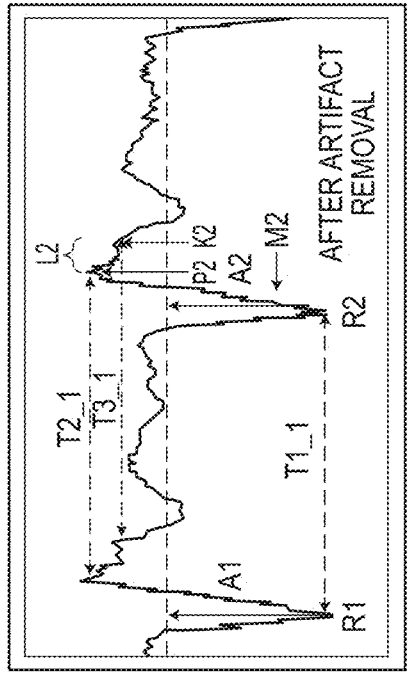
FIG. 7A
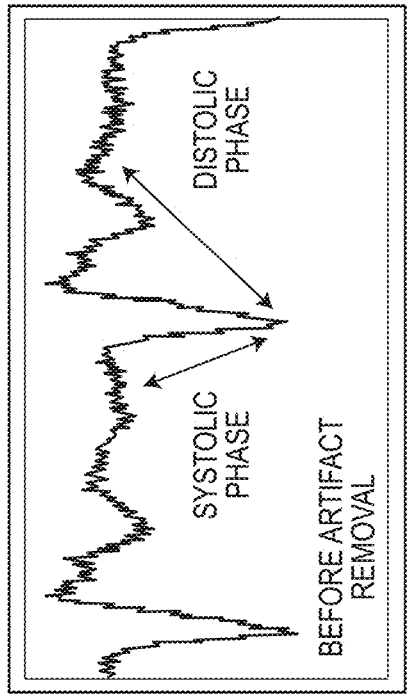
FIG. 7B
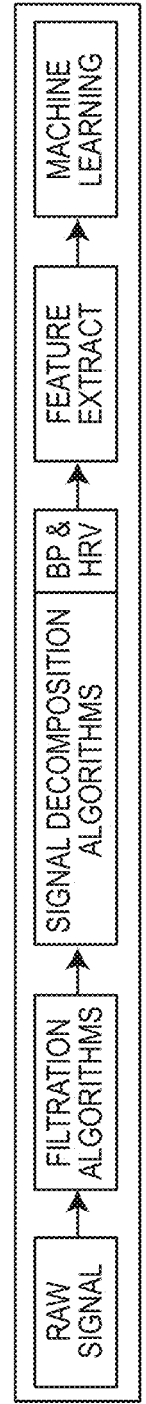

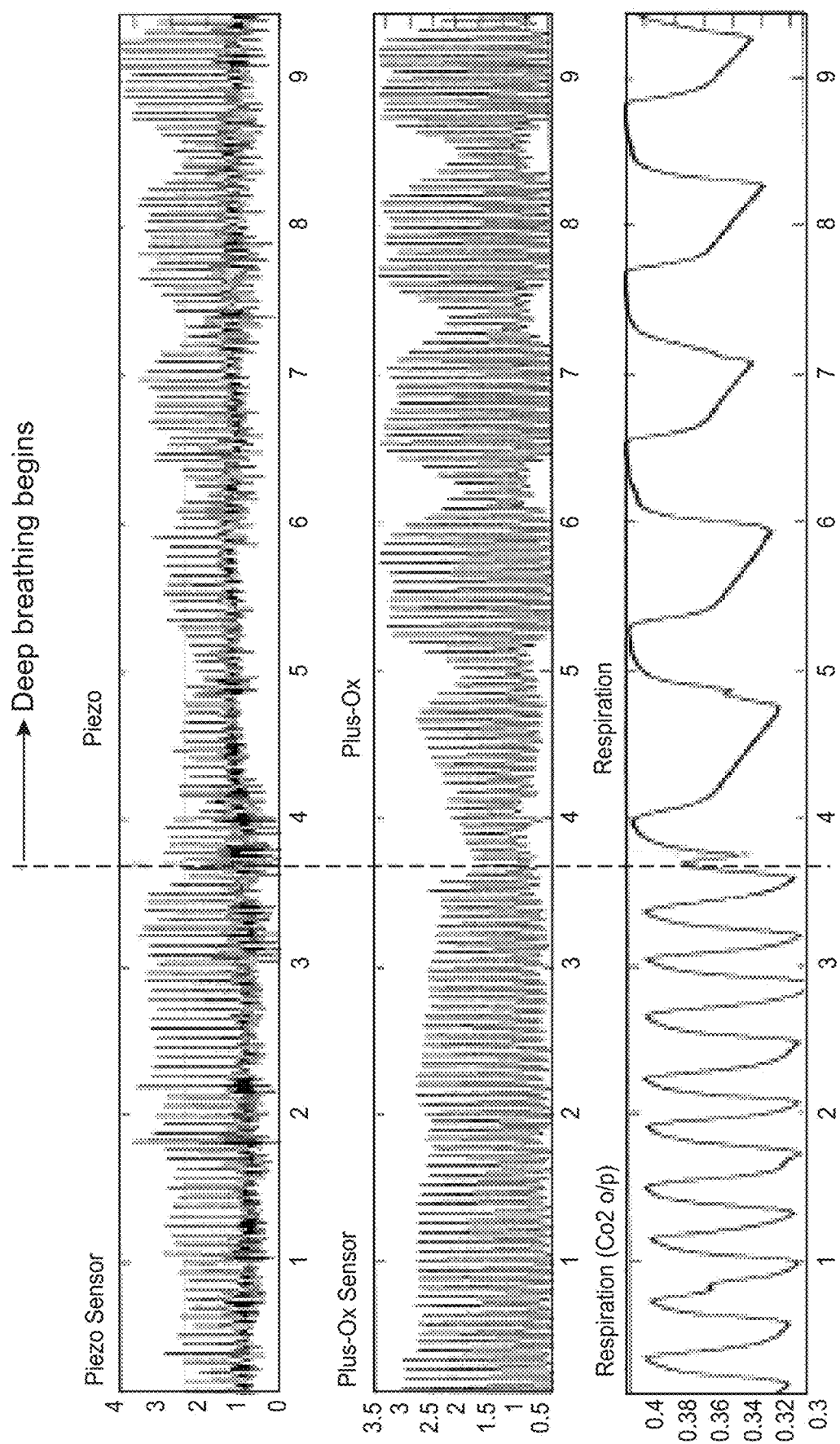
FIG. 13E Deep Breathing

Fast Breathing

BP Cuff inflation and deflation

MINIATURE PIEZOELECTRIC CARDIOVASCULAR MONITORING SYSTEM

CROSS-REFERENCE TO RELATED APPLICATIONS

This application claims priority to U.S. Provisional Application No. 61/972,750, entitled "Miniature Piezoelectric Cardiovascular Monitoring System," filed Mar. 31, 2014, which is hereby incorporated herein in its entirety.

FIELD OF THE INVENTION

The present disclosure relates to wearable health related monitors and, more particularly, to techniques for gathering blood pressure, flow data, and/or other cardiovascular variables via a wearable sensor assembly.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cardiovascular diseases are the most common cause of death worldwide. Currently, there are no effective portable and low-powered devices or systems that can be used for the non-invasive continuous monitoring of the cardiovascular system. The monitoring and treatment of medical and surgical conditions such as sepsis, congestive heart failure, hypertension, trauma, and other acute and chronic diseases could tremendously benefit from devices that allow direct or indirect continuous monitoring of important cardiovascular parameters in a nonintrusive manner. For example, monitoring cardiovascular parameters such as blood pressure waveform analysis (BPWA) and derivatives such as pulse pressure variability (PPV), or heart rate complexity changes such as heart rate variability (HRV) or respiratory rate (RR), or event dynamic changes in arterial vessel wall stiffness and the like could lead to effective measures for analyzing physiological conditions. That's because, at least in part, features extracted from these cardiovascular parameters have been shown to be highly correlative with a number of physiological conditions. Therefore, an effective technique for monitoring could provide caregivers with a variety of valuable clinical decision-making tools.

Yet, current techniques for continuous blood pressure (BP) and blood pressure waveform measurement are problematic. The techniques are invasive and confined to stationary complex clinical settings such as the intensive care unit (ICU). Hence, the techniques are not suitable for a wide range of applications, including personal healthcare monitoring.

Non-continuous monitoring systems have been proposed, but these too are problematic. Some of these non-continuous monitoring systems are relatively portable and non-invasive. However, they fail to provide the true waveform data of blood pressure and vascular tone (i.e., the degree of constriction experienced by a blood vessel relative to its maximally dilated state). Instead, these conventional techniques, whether from limitations in sensor sensitivity or limitations in data analysis, produce a reduced waveform data. They are incapable of producing true waveforms resulting from vascular wall movement or motion that are reflective of vascular tone, which are, as we show with the novel techniques described below, highly informative and rich with extracted clinically-useful information. Moreover, the majority of current noninvasive systems are cumbersome, since inflation of their mechanical cuff (or balloon) obstructs the normal everyday activities of life for the users. The systems are not usually wearable; and the information they provide lacks the frequency and granularity in which to take advantage of advances in the fields of signal processing and artificial intelligence. Further still, conventional noninvasive systems have been demonstrated to become inaccurate when patient physiology is labile, as occurs in critical states like hemorrhage or sepsis.

In light of these limitations and given the increased need for health care delivery models, there is a strong need to develop low-cost wearable monitoring systems that can span from the home to the hospital and that are capable of providing deeper physiologic information that help both health care providers and patients manage disease states in a more real-time fashion.

SUMMARY

In an embodiment, an apparatus comprises: a wearable sensor assembly including a flexible band having a polymer layer and a sensing layer both positioned for mounting the wearable sensor onto a sensing region of a subject for measuring vascular wall motion and blood flow dependent measurements over the sensing region, the wearable sensor comprising: (i) a piezoelectric sensor for measuring raw signal data, in real time, of vascular wall motion and blood flow dependent measurements, wherein the piezoelectric sensor comprises a piezoelectric electrode structure in the sensing layer for measuring the raw signal data in response to physical movement of the sensor region as detected by the piezoelectric sensor, and (ii) a secondary sensor for collecting and extracting photoplethysmograph derived blood flow data and photoplethysmograph derived waveform features; and a signal processor configured to receive the raw signal data from the piezoelectric sensor, filter the received raw signal data from the piezoelectric sensor, perform signal decomposition on the filtered raw signal data from the piezoelectric sensor, analyze the received raw signal data from the piezoelectric sensor to extract one or more waveform features from the received raw signal data, and analyze the photoplethysmograph derived blood flow data and the photoplethysmograph derived waveform features from the secondary sensor and compare the analyzed blood flow data and the waveform features to the extracted one or more waveform features from the piezoelectric sensor to extract indicators of circulating vascular volume and/or vascular tone to characterize and/or predict vascular health of the subject for clinical decision making.

In yet another embodiment, a therapeutic delivery system for administering a therapeutic treatment to a subject, the delivery system comprises: an apparatus in accordance with the present teachings; and an administration system comprising a therapeutic delivery vehicle in communication with a therapeutic treatment processor that controls delivery of the therapeutic treatment in response to received patient status data, the therapeutic treatment processor containing the signal processor and coupled to receive the raw signal data from the piezoelectric sensor, in a closed loop manner, implemented to store the one or more extracted waveform features of the sensing region in the patient status data, and implemented to determine instructions for administering the therapeutic treatment, in response to the stored one or more extracted waveform features.

In another embodiment, an apparatus comprises a wearable sensor assembly including a flexible band having a polymer layer and a sensing layer both positioned for mounting the wearable sensor onto a sensing region of a subject for measuring vascular wall motion and blood flow dependent measurements over the sensing region. The wearable sensor comprises: (i) a piezoelectric sensor for measuring raw signal data, in real time, of vascular wall motion and blood flow dependent measurements, wherein the piezoelectric sensor comprises a piezoelectric electrode structure in the sensing layer, and measures the raw signal data in response to physic movement of the sensor region as detected by the piezoelectric sensor; and, in some examples, (ii) a secondary sensor for collecting photoplethysmograph derived blood flow data. The apparatus further comprises a signal processor configured to receive the raw signal data from the piezoelectric sensor, filter the received raw signal data from the piezoelectric sensor, perform signal decomposition on the filtered raw signal data from the piezoelectric sensor, extract one or more features of the sensing region from the received raw signal data from the piezoelectric sensor, and analyze the blood flow data from the secondary sensor to extract indicators of circulating vascular volume and vascular tone.

In another embodiment, a therapeutic delivery system for administering a therapeutic treatment to a subject comprises the apparatus as described above and an administration system comprising a therapeutic delivery vehicle in communication with a therapeutic treatment processor that controls delivery of the therapeutic treatment in response to received patient status data. The therapeutic treatment processor contains the signal processor, is coupled to receive the raw signal data from the piezoelectric sensor, in a closed loop manner. The therapeutic treatment processor is implemented to store the one or more extracted features of the sensing region in the patient status data, and is implemented to administer the therapeutic treatment in response to the stored one or more extracted features.

In yet another embodiment, a therapeutic delivery system for administering a therapeutic treatment to a subject comprises the apparatus as described above and an administration system comprising a therapeutic delivery vehicle in communication with a therapeutic treatment processor that controls delivery of the therapeutic treatment in response to received patient status data. The therapeutic treatment processor is coupled to the signal processor to receive the one or more extracted features of the sensing region and is implemented to: (i) store the one or more extracted features of the sensing region in the patient status data, and (ii) administer the therapeutic treatment in response to the stored one or more extracted features.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 3A illustrates a plot of raw signal data measured by the piezoelectric sensor of FIGS. 2A and 2B, while

FIGS. 7A and 7B illustrate a segment of the raw signal data before and after artifact removal, respectively, where in FIG. 7B, the segment has been analyzed for data extraction, as may be performed in accordance with the signal process of FIG. 4;

FIGS. 13A-13G illustrate plots of raw data collected from the piezoelectric sensor and used for extracting physiological conditions under different conditions of a subject;

DETAILED DESCRIPTION

In some examples, the present techniques allow for measuring raw signal data using a piezoelectric sensor device. The techniques may be used for extracting physiological conditions from raw signal data collected from the piezoelectric sensor device and, in some examples, from one or more additional sensor devices, embedded in a wearable device.

Figure 1:
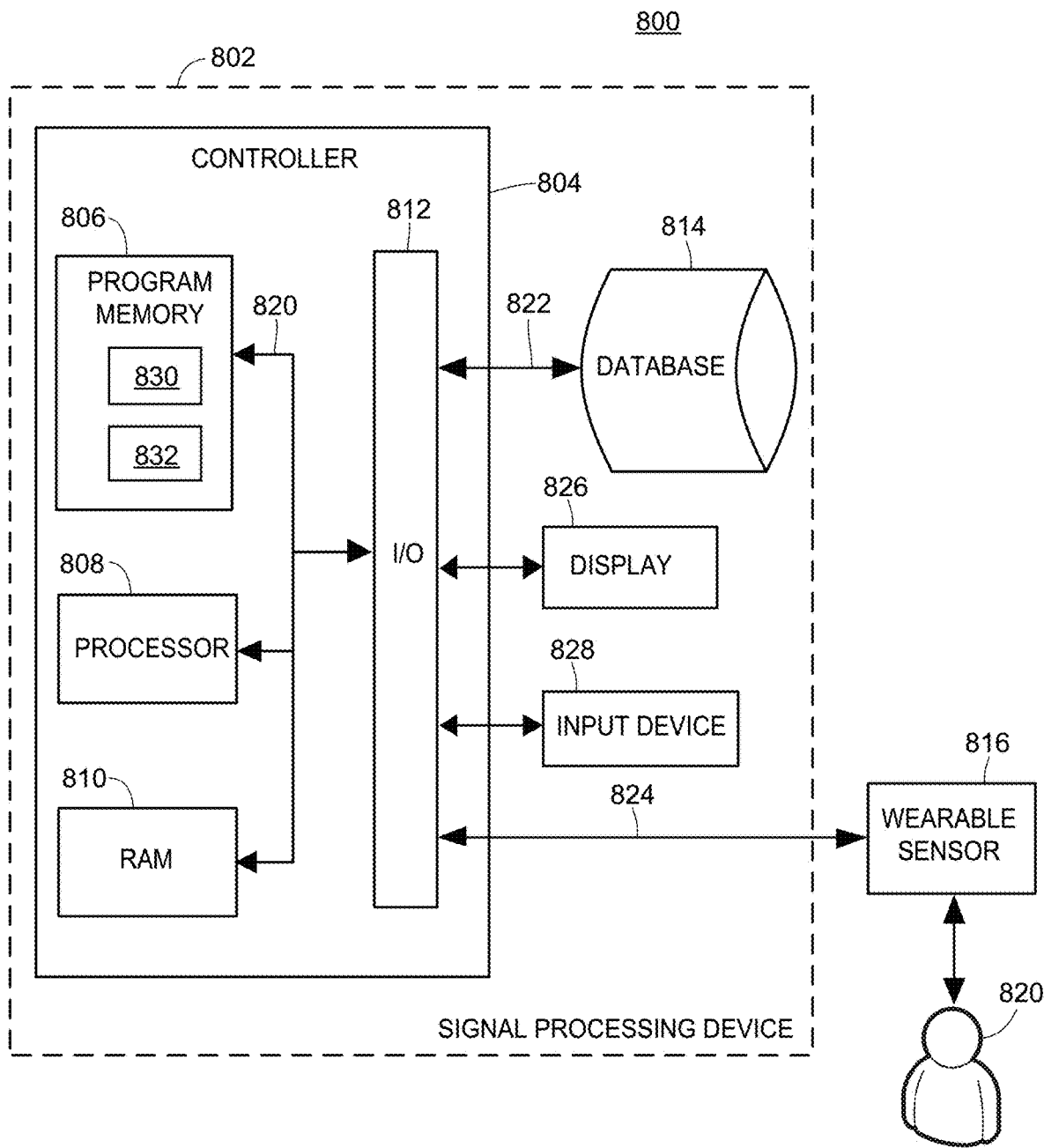
FIG. 1 is a schematic view of an apparatus for measuring raw signal data using a piezoelectric sensor-based device and for extracting physiological conditions from the raw signal data.

FIG. 1 is an example block diagram 800 illustrating the various components used in implementing an example embodiment of a piezoelectric cardiovascular monitoring system discussed herein. A signal-processing device 802 (or "signal processor") may be coupled to a patient 820 via one or more wearable sensors 816 (or a "wearable sensor assembly") in accordance with executing the functions of the disclosed embodiments. The signal-processing device 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, one or more processors 808 (may be called microcontrollers or a microprocessors), a random-access memory (RAM) 810, and the input/output (I/O) circuit 812, all of which are interconnected via an address/data bus 820. It should be appreciated that although only one processor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824, which may include one or more wired and/or wireless (Bluetooth, WLAN, etc.) connections, may operatively connect the controller 804 to a wearable sensor 816 through the I/O circuit 812. The wearable sensor 816 may be operatively connected to the patient 820. Further details of an example wearable sensor, or wearable sensor assembly, are included in reference to FIG. 2A, FIG. 2B, and FIG. 2C.

The program memory 806 and/or the RAM 810 may store various applications (i.e., machine readable instructions) for execution by the processor 808. For example, an operating system 830 may generally control the operation of the signal-processing device 802 and provide a user interface to the signal-processing device 802 to implement the process 100 described herein. The program memory 806 and/or the RAM 810 may also store a variety of subroutines 832 for accessing specific functions of the signal-processing device 802. By way of example, and without limitation, the subroutines 832 may include, among other things: a subroutine for taking measurements with the wearable sensor 816, a subroutine for filtering measurement (or data) from the wearable sensor 816, a subroutine for performing signal decomposition on raw signal data from the wearable sensor 816, and a subroutine for extracting one or more features of a sensing region from the raw signal data from the wearable sensor 816. The subroutines 832 may also include other subroutines, for example, implementing software keyboard functionality, interfacing with other hardware in the signal-processing device 802, etc. The program memory 806 and/or the RAM 810 may further store data related to the configuration and/or operation of the signal-processing device 802, and/or related to the operation of the one or more subroutines 832. For example, the data may be data gathered by the wearable sensor 816, data determined and/or calculated by the processor 808, etc. In addition to the controller 804, the signal-processing device 802 may include other hardware resources. The signal-processing device 802 may also include various types of input/output hardware such as a visual display 826 and input device(s) 828 (e.g., keypad, keyboard, etc.). In an embodiment, the display 826 is touch-sensitive, and may cooperate with a software keyboard routine as one of the software routines 832 to accept user input. It may be advantageous for the signal-processing device 802 to communicate with a broader medical treatment network (not shown) through any of a number of known networking devices and techniques (e.g., through a commuter network such as an hospital or clinic intranet, the Internet, etc.). For example, the testing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 1, it is understood that any or the entire signal processing functionality and/or components of the signal-processing device 802 may be combined with a wearable sensor assembly, such as the wearable sensor 816. In this manner, a wearable sensor may both gather data about the patient 820 and process the gathered data to extract one or more waveform features, as discussed further below. Also, although depicted as a single component in FIG. 1, the wearable sensor 816 may include multiple of the same type or different types of sensors. For example, the wearable sensor 816 may include both a piezoelectric sensor for measuring raw signal data and a secondary sensor for collecting photoplethysmograph derived blood flow and hemoglobin oxygen saturation data. Generally, the wearable sensor 816 may include one or more piezoelectric sensors or electrodes, as further discussed with reference to FIG. 2A, FIG. 2B, and FIG. 2C. In some examples, the wearable sensor 816 may be implemented with one or more of a variety of other (or secondary) sensors, such as temperature sensors, motion sensors, actigraphy sensors, galvanic skin response sensors, impedance sensors, etc.

In a case in which the wearable sensor 816 includes a secondary sensor for collecting photoplethysmograph derived blood flow data, the secondary sensor may provide (e.g., to a signal processing computer) a waveform that is flow related. The changes in the waveform may provide information related to the arterial tone at both the site of measure and, in some cases, more centrally. Changes in the waveform from the secondary sensor along with changes in a waveform from the piezoelectric sensor (amplitude, width, time differences in peaks, delta responses to provocative movements such as breathing, volume infusion, etc.) may provide complementary information about the patient as it relates to circulating vascular volumes and vascular tone. Thus, the ability to look at these two signals together allows for determining which components are responsible for changes and as well as how best to favorably affect changes, such as providing medications to tighten or relax arterial wall tone. An example implementation of the wearable sensor 816 as a two-sensor device is shown in FIG. 14.

In the example of a motion sensor, the signal-processing device 802 may be used in measuring motion data for changes in motion of the wearable sensor in response to changes in the location or orientation of the sensing region and/or of the subject. With this data, the signal-processing device 802 may extract motion artifacts and suppress or even cancel noise in the raw signal data based on that motion data. In some examples, the motion sensor may be implemented as a gyroscopic sensor or an accelerometer imbedded within the wearable sensor 816.

Figure 2A:
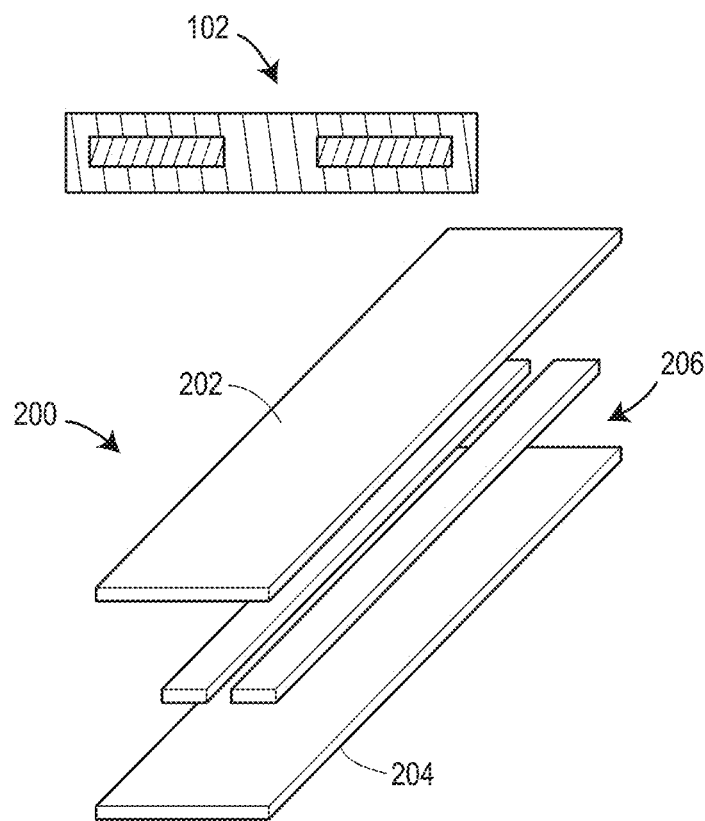
FIGS. 2A and 2B illustrate an example implementation of a wearable sensor device as may be used in the apparatus of FIG. 1.
Figure 2B:
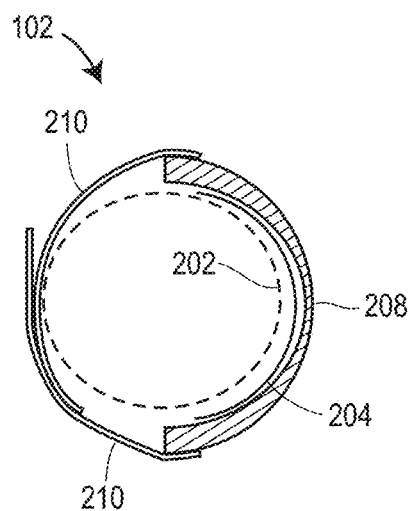
Figure 2C:
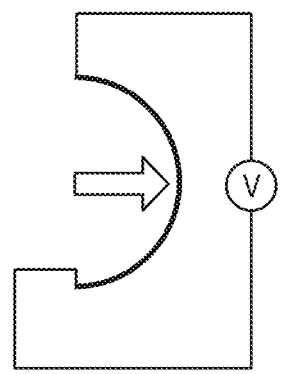
FIG. 2C is a circuit level illustration of the piezoelectric operation of the wearable sensor device of FIGS. 2A and 2B.

As illustrated in FIGS. 2A and 2B, wearable sensor 102 includes a thin piezoelectric sensor (or sensor assembly) 200 that is capable of measuring raw signal data that alters in response to blood pressure changes in a subject. In some examples, the sensor 200 is triggered manually, or in other examples a controller triggers the sensor automatically.

Implemented in a wearable device, the sensor may be triggered, in some examples, by a device user accessing software a sensor controller, for example, through a touchscreen or other input device. In some examples, the sensor 200 may be a continuous sensor that collects raw signal data continually and accurately, irrespective of changes in the subject's physiological state, position, etc.

In the illustrated example, the wearable device 102 is adapted to be placed around a subject's finger, as shown in FIG. 2B. The piezoelectric sensor 200 is a multilayer structure formed of a first compliant polymer layer 202, a second compliant polymer layer 204, and an electrode layer 206 therebetween. The polymer layers 202 and 204 provide a contact surface for the sensor 200 to measure raw data correlative to changes in blood pressure. In FIG. 2B, for example, the layer 202 is proximal to a subject's finger and provides a sensing surface, while the layer 204 is disposed distally and adjacent a reference substrate 208, in the form hard backing curved substrate designed to extend at least partial around the subject's finger. The hard backing substrate 208 may be held in place by a strap 210 (such as Velcro, constant tension spring, small inflatable cuff, glove, or other adjustable band) or other suitable restraint, for example. The hard backing substrate 208 provides stability to maintain the sensor 200 in place during continual measurements and also provides a reference plane from which the highly sensitive raw data signal monitoring of the sensing surface of layer 202 can be achieved.

The electrode layer 206 may include one or more piezoelectric sensors. In the illustrated example, the electrode layer 206 includes tow piezoelectric electrodes (212 and 214) that extend the longitudinal length of the sensor 200 providing a sensing region that extends along a length of the subject's finger. The electrodes 212 and 214 are spaced apart by sufficiently small distance to facilitate highly sensitive raw data measurements under a force applied to the sensing layer 202, and resulting in a measurable change in a sensed voltage as shown in the circuit level depiction of FIG. 2C. This applied force, which is isolatable from other potential forces affecting the subject's finger, is due to blood pressure and/or blood flow changes in the subject, which are measured as the highly accurate raw signal data. Each piezoelectric electrode 212 and 214 functions as a sensor, while the combination of the two (or more) can provide more accurate results as output values are combined and signal processed. Additional numbers of sensors may be used, for example, formed of parallel and co-extensive strips of piezoelectric electrodes. In other examples, the piezoelectric sensors may be of different lengths to one another, or at least not all the same length. Moreover, in some examples, the electrodes are not parallel. For example, the electrodes herein may form a crossing pattern or a mesh pattern. The electrodes, for example, may be in crossing array configuration, which would have the benefit of offering mapping of the resulting blood pressure data from the sensor. The electrodes may be formed of any suitable known piezoelectric materials, such as Gold (Au), Indium Tin Oxide (ITO). Other example known piezoelectric materials include quartz, aluminium nitride, apatite, barium titanate, lithium tantalate, lead zirconate titanate, lead scandium tantalate, lanthanum gallium silicate, bimorph, unimorph, gallium phosphate, polyvinylidene fluoride, and potassium sodium tartrate. The electrodes may be plate-like structures, as such, or wire-based structures. In some examples, the electrodes are individually formed and placed between the polymer layers. In some examples, the electrodes are patterned formed directly on a polymer layer. The polymer layers may be formed of a polyvinylidene fluoride (PVDF), for example. The piezoelectric sensor 200 has been tested at sensitivity levels (measured in $\mu V/Pa$) between 10 $\mu V/Pa$ to 100 $\mu V/Pa$, in some examples. These sensitivity levels are orders of magnitude better than those reported for capacitive, microfluidics based sensors and conventional piezoelectric devices. In some examples, sensor position may be calibrated based on position and/or structure. In some examples, pressure, bending, or torsion measurements may be made by corresponding sensor techniques to further this calibration.

In any event, while two piezoelectric electrodes are shown, one strip may be used or additional strips may be used, for example to improve sensor response and improve signal reliability in the presence of motion or positioning uncertainty of the subject. Each surface of the piezoelectric electrodes 212 and 214 may be formed of a thin piezoelectric polymer (PVDF) coated with a metal electrode material.

The two polymer layers 202 and 204 may be formed of the same material and exhibit the same compression and tensile strength profiles. In this way, both layers may operate similarly under plastic deformation from the applied force at the layer 202. However, in other examples, the polymer layers 202 and 204 could be formed of different polymer materials or different thicknesses, etc. to create a relative difference in compression and/or tensile strength profiles between the layers 202 and 204. In this way, the piezoelectric sensor 200 may be designed to achieve a desired level of accuracy in raw data and with an ability to amplify or de-amplify force measures obtained at the sensing layer 202.

The sensor 200 is, in part, capable of continuous blood pressure waveform or vascular tone measurement due to the implementation of piezoelectric electrodes 212 and 214 to produce a time history of blood pressure of a subject. While the sensor 200 is shown applied to a subject's finger, the sensor 200, and the wearable device 102, more broadly, may be applied to other areas of a subject such as the wrist, head, ankle, waist, arm, leg, neck, chest, waist, etc. For example, when used on the wrist, the sensor 200 may be entirely secured within an adjustable band, that extends around the entire wrist. An example implementation would be a wearable health monitoring device.

The wearable health-monitoring device may be a device, such as a wireless-enabled bracelet type activity tracker, specially configured for gathering highly accurate and health-related raw signal data via the piezoelectric electrodes 212 and 214. Alternatively, the sensor 200, including the piezoelectric electrodes 212 and 214, may be integrated in a wearable computing or communication device, such as a smartwatch or other watch or wristband configurable to be connected (e.g., via Bluetooth) to a smartphone, tablet computer, laptop computer, etc. In such cases, the signal processing functionality of the signal processing computer 802 may be integrated into the wearable computing or communication device or may be divided between the wearable computing or communication device and another wirelessly connected computing device. In another example, when used on the head of a patient, the sensor, including the piezoelectric electrodes 212 and 214, may be integrated into a head-mounted wearable computer (e.g., a wearable computer configured to be operated in a smartphone-like hands-free manner), where the piezoelectric electrodes 212 and 214 are located adjacent to a temple of a patient.

Further, the sensor 200 may be integrated in a non-wearable computing or communication device, in an implementation. For example, the highly accurate raw signal gathering capabilities of the sensor 200 (e.g., via the piezoelectric electrodes 212 and 214) may be integrated with a smartphone, tablet computer, laptop computer, etc. In such a case, the sensor 200 may be disposed along an edge or surface of the non-wearable computing or communication device such that a patient may selectively place portions of their body (e.g., finger, wrist, etc.) proximate to the integrated sensor 200 for raw signal data retrieval via the sensor 200. In yet other examples, the sensor 200 may be integrated with these devices through a connected peripheral sensing device.

In other examples, the wearable device 102 may be implemented as a sandwiched polymer/piezoelectric structure that is adhesively mounted to a subject, such as at a subject's temple, periauricular area, nasal bridge, or other region when raw data correlative of blood pressure/blood flow may be accurately monitored.

For any of these implementations, small deformations of the piezoelectric layer 206 induced by pressure from the underlying blood vessel produces a differential voltage output.

Figure 3A:
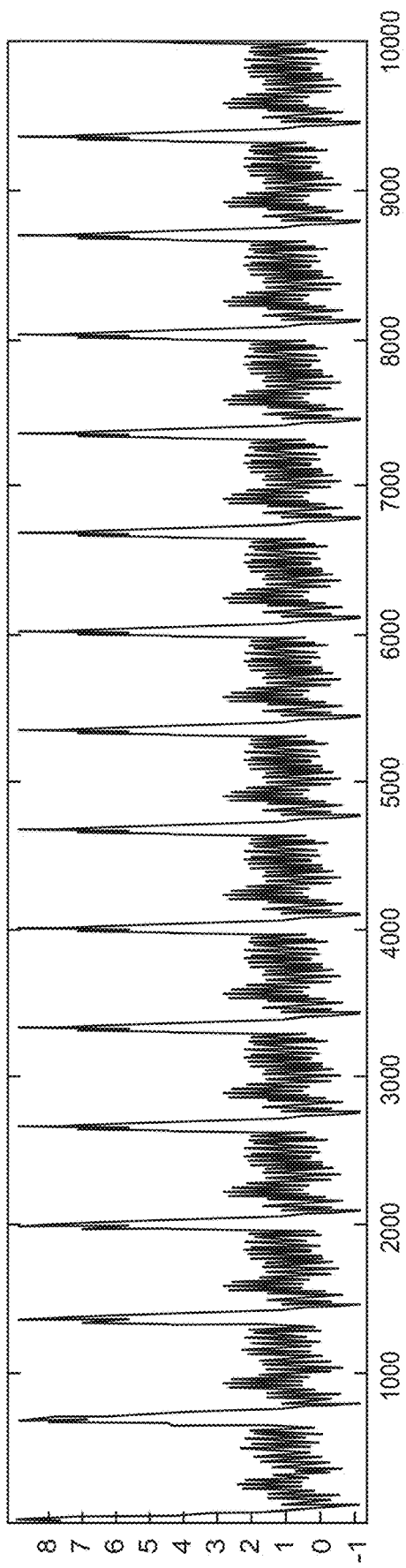
Figure 3B:
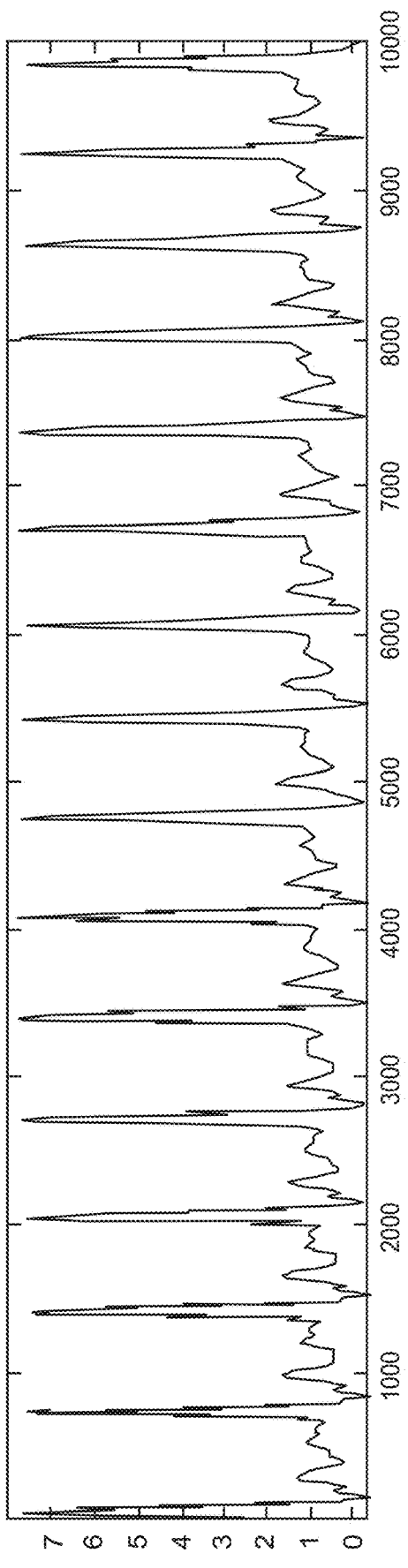
FIG. 3B illustrates a plot of the same raw signal data after initial filtering.

In operation, pressure on the sensing layer 202 produces a combination of compressive and bending deformation. The piezoelectric effect within the material, i.e., layer 206, causes an electric displacement across the thickness of the piezoelectric layer that is proportional to a combination of the axial and radial strains in the material. As shown in FIGS. 3A and 3B, the piezoelectric sensor 200 is able to produce a continual detailed record of pressure over time, where the raw data collected by the sensor 200 may be measured electronic recording instruments, such as an oscilloscope or other device as the signal-processing device 802. FIG. 3A illustrates the raw signal data the wearable device 102 communications to the signal-processing device 802, and as may be displayed prior to any signal filtering. FIG. 3B illustrates the raw signal data after an initial filtering by the signal-processing device 802.

The piezoelectric sensors described herein may be capable of providing a passive transduction mechanism, small in size, with high sensitivity, and flexible use. The sensors offer substantial advantages over existing blood pressure measuring systems, in this way. Moreover, the piezoelectric electrodes require no external power supply, while the resulting raw signal data exhibits high signal-to-noise ratio, even without external amplification of the signal.

To facilitate measurement, in addition to piezoelectric electrode spacing, the electrodes 212 and 214 can be on the order of just a few millimeters in cross-sectional thickness, allowing for non-invasive use that is much less cumbersome than existing blood pressure monitors. The use of a very thin piezoelectric layer 206 results in high sensitivity to blood pressure, while allowing flexibility to shape the sensor around fingers and wrists of varying size.

Figure 4:
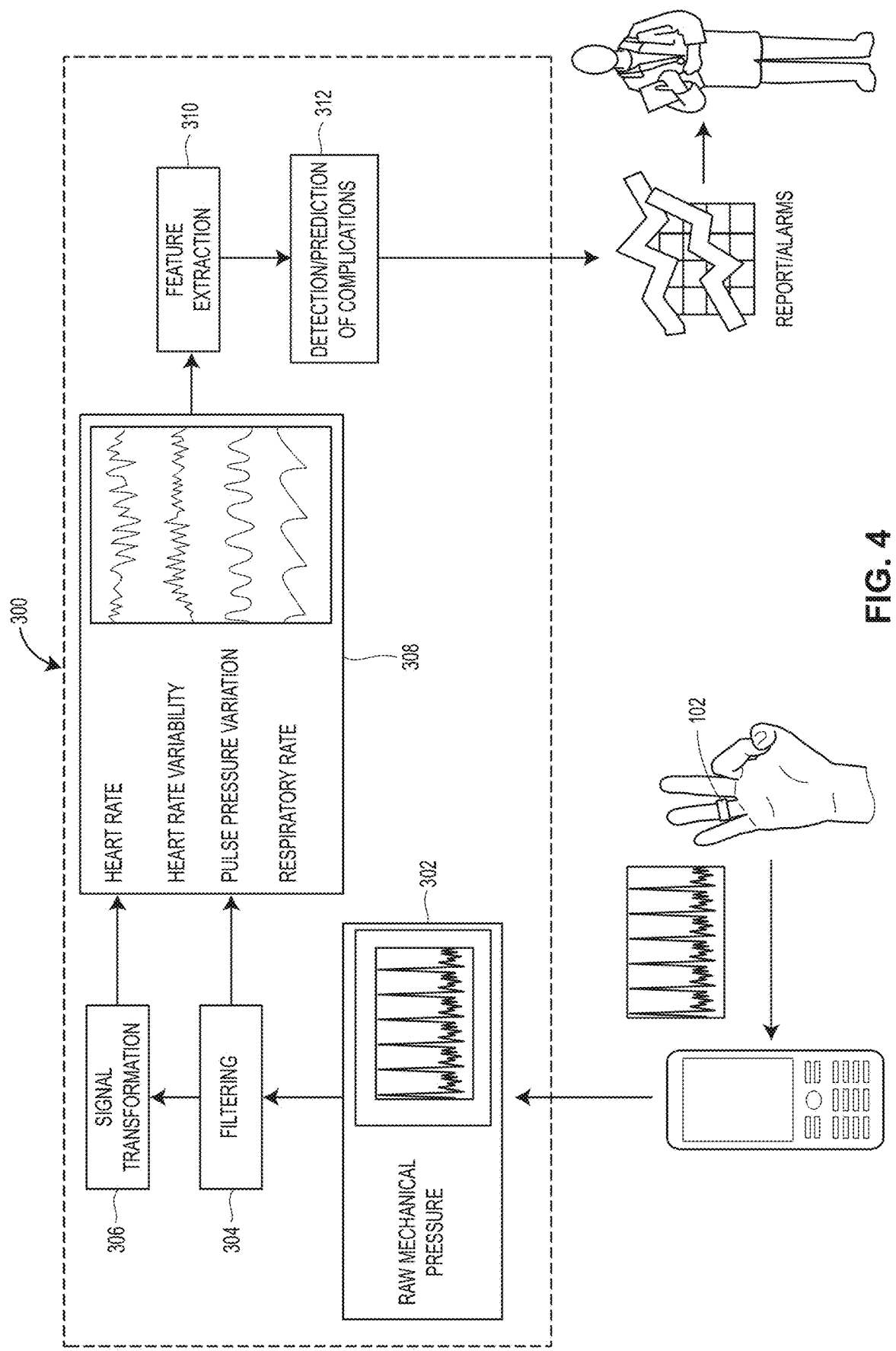
FIG. 4 is a schematic diagram of a signal processor implemented in the apparatus of FIG. 1 to extract the physiological conditions, in accordance with an example.

FIG. 4 illustrates a signal processing system 300 capable of extracting one or more physiological conditions from the raw signal data of the wearable device 102. The system 300 is discussed in reference to example processes 400 and 500 in FIGS. 5 and 6, respectively. The processes 400 and 500 differ in the type of sensor inputs that may be applied and therefore in the number of waveform features that may be extracted from the raw signal data. But otherwise the processes 400 and 500 are similar; and therefore, like reference numerals are used.

Figure 5:
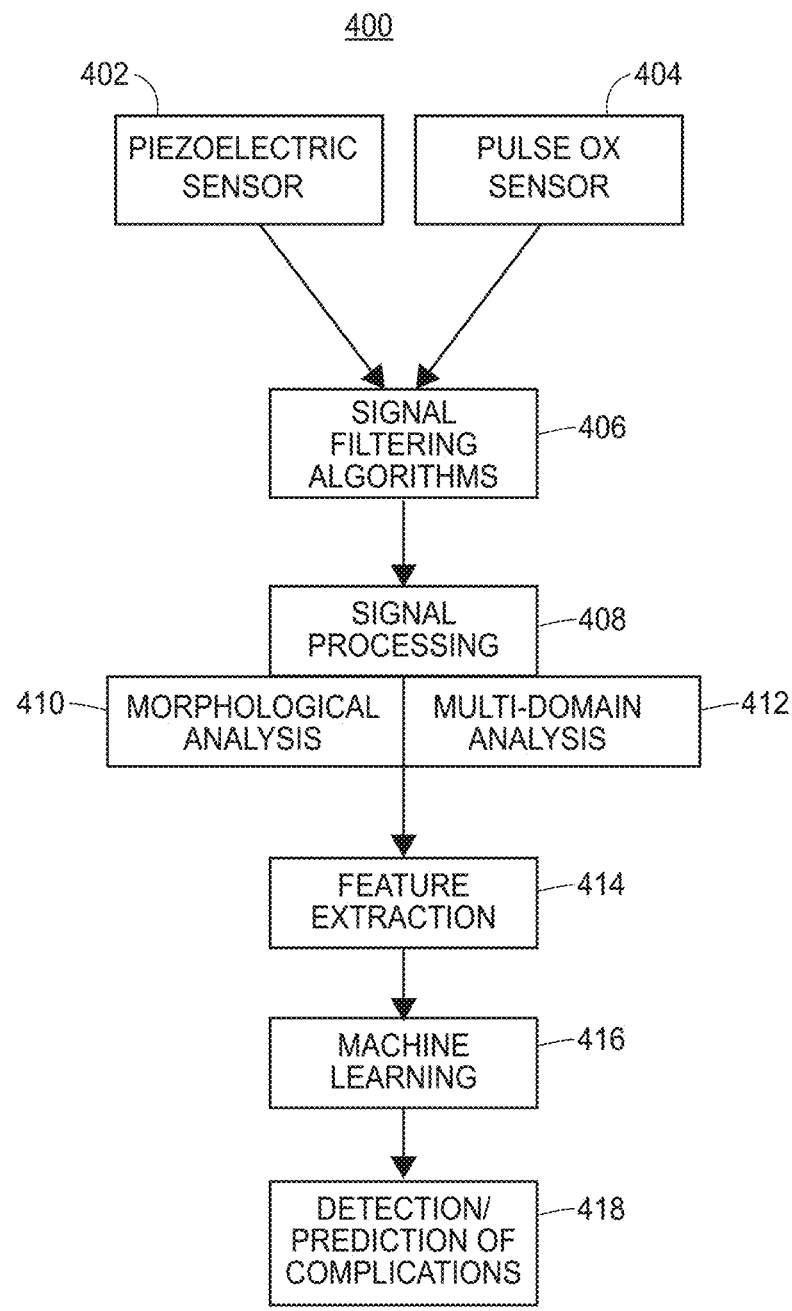
FIG. 5 is a flow diagram of operation of signal processor of FIG. 4, in accordance with an example implementation of FIG. 1.

In reference to FIG. 5, at blocks 402 and 404 raw signal data from piezoelectric sensor 200 and a raw signal data from secondary sensor are provided to the signal processor system 300, for example through a wireless or wired interface. An example two sensor device, in the form of a piezoelectric sensor and pulse-oximetry sensor, is described further with reference to FIG. 14. Wired interfaces may include twisted pair, coaxial, ribbon, fiber optic, etc. cable facilitating communications via any suitable wired networking protocol, such as a protocol as standardized in IEEE 802.3. Wireless interfaces may include one or more wireless routers, modems, antennas, transceivers, etc., facilitating communications via any suitable wireless networking protocol, such as Bluetooth or a protocol standardized under IEEE 802.11. In some implementations, communications between the sensor 200 and the signal processor system 300 may follow a proprietary protocol or protocol specially configured for health-related or activity-tracking applications. The raw signal data is collected at a raw mechanical pressure converter 302, which provides the raw signal to a filtering stage 304 that applies signal filtering algorithms 406 of FIG. 5. In this way, the block 402 provides raw signal data, in real time, where that raw signal data is a blood flow dependent data measurement. The block 404 provides signal data from a secondary sensor, e.g., one collecting photoplethysmograph derived blood flow and hemoglobin oxygen saturation data, through the use of a radiative reflectance or radiative transmission signal.

Via a block 408, a transformation stage 306 performs a signal decomposition on the filtered, received raw signal data. Because of the high sensitivity of the wearable sensor 102 and the piezoelectric sensor 200, in particular, raw pressure signal inherently contains a multitude of vital information regarding a subject's physiological state. This decomposed signal data from the stage 306 and the filtered raw data from the stage 304 are provided to feature extraction analysis stage 308. The stage 308 contains algorithms for extracting any of a plurality of different waveform features from the received raw signal data. For example, the stage 308 may be designed to analyze raw signal data and extract any number of features from the waveform and thereby identify any number of physiological conditions expressive by one or more of the waveform features, including, but not limited to blood pressure (BP), pulse pressure (PP), pulse pressure variability (PPV), heart rate (HR), heart rate variability (HRV), arterial wall stiffness (AWS) or other vascular wall motion related features, blood flow (BF), and respiratory rate (RR).

To achieve feature extraction, the stage 308 may perform morphological analyses at a block 410 and multi-domain analyses at a block 412 to extract features that are provided (from both blocks) to a feature extraction module 310, via block 414. The stage 308 may access historical blood pressure or blood flow data or other previously-collected data correlative to physiological features such as blood pressure (BP), pulse pressure (PP), heart rate (HR), heart rate variability (HRV), arterial wall stiffness (AWS), blood flow (BF), pulse transit time (PTT) or respiratory rate (RR). That historical data may include data collected from different subjects, collected solely from the subject under examination, collected from a subset of subjects having common physiological features with the subject, or some combination thereof. Such data may be analyzed, at least in part, through morphological analysis block 410.

In performing the domain analysis of block 412, the stage 308 may perform raw signal data extractions by identifying one or more signal (waveform) features in the data. These signal features may include identifying global and local peaks and troughs within the raw signal data, as well as spacing distances (or periods) between features. FIG. 7A illustrates a segment of raw signal data before artifact removal. FIG. 7B illustrates the same segment, after artifact removal and after the stage 308 has performed raw signal data extractions, where at least some of the spacing distances (or periods) between features may be related to vascular wall reflections from the more proximal vasculature (portions of the aorta). These peaks, while arbitrarily labeled in FIG. 7B may vary in peak, width, and spacing to each other based on important changes in physiology and treatment.

The output voltage from the wearable device 102 may be linearly dependent on pressure, but the linear coefficient may vary based on ring location, position of the finger, and tightness of fit. As such, in some examples, physiological details are taken from the relative height of waveform features in the raw data signal and variation in the signal over time, as opposed to exclusively by absolute voltage output. What we've found, remarkably, is that the actual mechanical properties of the movement of the arterial wall can be measured producing incredible waveform information similar (and for some features enhanced) to that produced by an indwelling catheter in the artery measuring pressure changes.

In any event, the particular features to be extracted by the stage 308 may be selected as those that are considered important pre-cursors in the monitoring of a subject's physiological condition. The selected extracted features, therefore, may provide valuable insights into the abnormalities of the morphology of the pressure signal to help identify disease cases. In some examples, the extraction data from block 414 may be provided to a block 416, also implemented in stage 310, where machine learning may be performed to optimize feature extraction and data analysis. Example machine learning implementations include decision tree learning algorithms, clustering algorithms, support vector machine algorithms, pattern recognition algorithms, feature selection algorithms, and others known to those skilled in the art.

In particular, signal processors may optimize and/or detect time-based waveform features in raw signal data via machine learning techniques. A signal processor may detect all peaks in a raw signal using a hierarchical method that applies a derivative of the original signal to the raw signal. The timing between all peaks as well as the relative amplitudes of the peaks within the same pulse may be calculated. The signal processor may aggregate and use these values as features directly calculated from time signal.

Further, signal processors may utilize transform-based techniques to optimize and/or detect features in raw signal data. A signal processor may transform a windowed portion of the raw signal data into other domains using transforms, such as Stockwell transforms (S-transform) and/or Dual Tree Complex Wavelet Transforms (DTCWT). Then, for any given window, the signal processor may extract multiple features in each domain. For instance, entropy of DTCWT coefficients or the statistical averages on the max frequencies across the window may be extracted. It is clear however that any suitable features and number of features may be extracted in each domain.

Signal processors may also utilize machine learning, based on extracted features, to predict physiological events/complications. Feature, such as those discussed above, or subset of features may be input to a machine learning algorithm, which is trained to predict one or more targeted physiologic events, such as hemorrhagic shock. By example and without limitation, such a machine learning algorithm may utilize SVM, Random Forest, Neural Networks, ECOC combined with SVM, and ensemble classifiers to predict the one or more targeted physiologic events.

In some examples, the system 300 takes the extracted data from stage 310 and performs morphology detection and/or prediction a subject using a stage 312 and at a block 418. The output data from the stage 312 may be displayed as a health report and/or alarm condition, for example, using the display 826 of signal-processing device 802, a health report and/or alarm condition may be displayed as a web page, mobile alert, tactile alert or alarm (e.g., via a vibrating function of a smartwatch or smartphone), or any other suitable visual and/or tactile display. While in other examples, the output data is provided to a treatment system, such as therapeutic delivery system for administering a therapeutic treatment to a subject. That delivery system may include an administration system having therapeutic delivery vehicle in communication with a therapeutic treatment processor that controls delivery of the therapeutic treatment in response to received patient status data. In this way the system 300 may be part of a closed loop system with a treatment system, where the latter is design to administer a therapeutic treatment in response to the stored one or more extracted features from the former.

Figure 8:
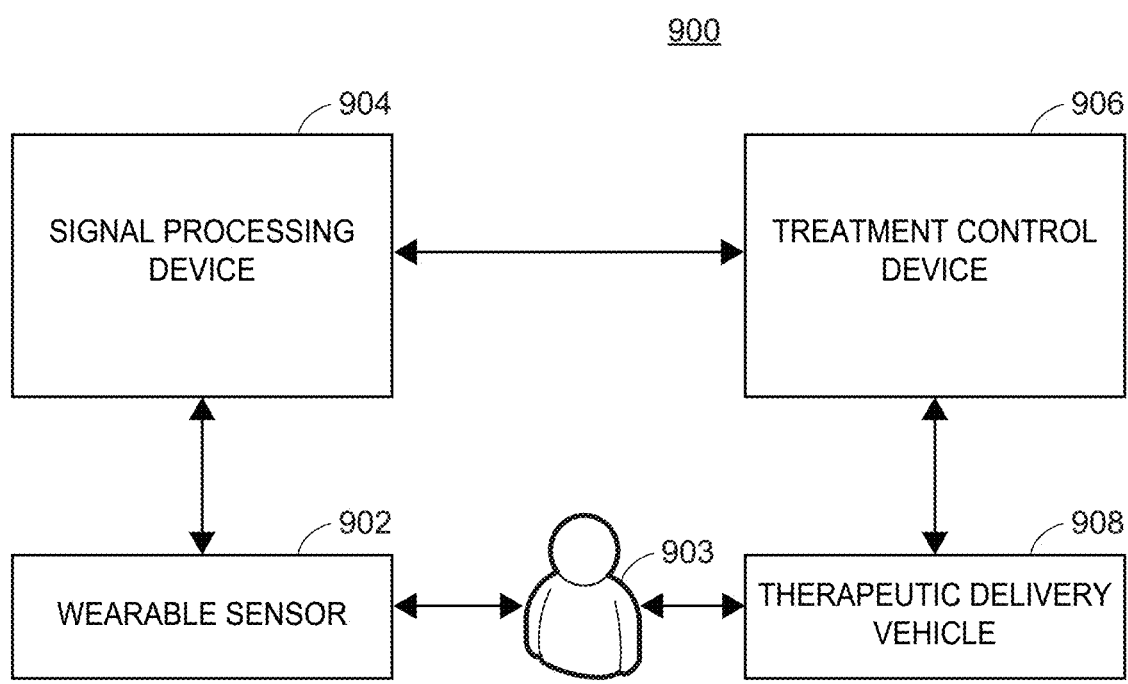
FIG. 8 is a schematic of a therapeutic delivery system for administering a therapeutic treatment to a subject using the apparatus of FIG. 1 in a closed loop manner.

FIG. 8 illustrates an example closed loop system 900 in which a therapeutic treatment may be administered in response to a stored one or more extracted features. A wearable sensor assembly 902, in accordance with the teachings herein, is attached to a subject 903. The sensor assembly 902 measures blood pressure through a piezoelectric sensor within the assembly 902. In dual (or multiple) sensor devices, the assembly 902 further measures blood flow using a secondary sensor of the assembly 902. In some examples the wearable sensor assembly 902 includes plurality of sensors, including one or more of a temperature sensor, a motion sensor, an actigraphy sensor, a galvanic skin response sensor, an impedance sensor, or any combination thereof.

A signal-processing device 904, having one or more processors and one or more memories, is coupled to the assembly 902 to perform such operations as receiving raw signal data, filtering the received raw signal data, perform signal decomposition on the filtered raw signal data, extracting one or more features of the sensing region, and analyzing blood flow data, and extract indicators of circulating vascular volume and vascular tone.

The signal-processing device 904 is configured to automatically analyze the wearable sensor data and compare that data to recently-recorded or historically-recorded data to allow for more accurate analysis of the signal data. The signal-processing device 904 may determine, from the analyzed data, characteristics such as subject (903) stress level, presence of hypertension, a syncope or hypotension susceptibility and warning, the presence of Raynauds disease, the presence of potential sickle cell disease, sepsis, shock, sleep apnea, respiratory state (asthma, COPD exacerbations) and even whether a patient has had a cardiac arrest and other conditions expressed by blood flow levels and/or changes thereto.

The signal-processing device 904 is coupled to a treatment control device 906 that determines a treatment regimen based on the received processed data. The treatment control device 906 may be an existing treatment device, such as an infusion pump, that controls a therapeutic delivery vehicle 908 capable of delivering a blood pressure medication (vasopressors such as norepinephrine or vasodilators such as nitroprusside), sedation agents, volume expanders, and others. The signal-processing device 904 could be made part of an extracorporeal circuit such as a dialysis machine that could adjust flow if the sensor and signal-processing device predicted the near occurrence of a drop in blood pressure. Similar strategies could be developed for other treatment control devices like mechanical ventilators that allow adjustment of ventilation parameters based on their effects on the sensor data. For example, the signal-processing device 904 may be configured to identify local peaks in the received data from the sensor (including peak data for each different sensor type within the sensor) and from a difference in peak values determine a vascular volume and/or vascular tone.

The process 400 may include performing feature extraction (414), the optional machine learning (416), and/or the optional morphology detection/prediction (418), using demographic and related health information of the user, where available. Either way, the machine learning algorithm of block 416 may assess the extracted features, predict the progression and occurrences of critical states and in conjunction with the block 418 provide clinical recommendations to care givers as well as to patients themselves.

Figure 6:
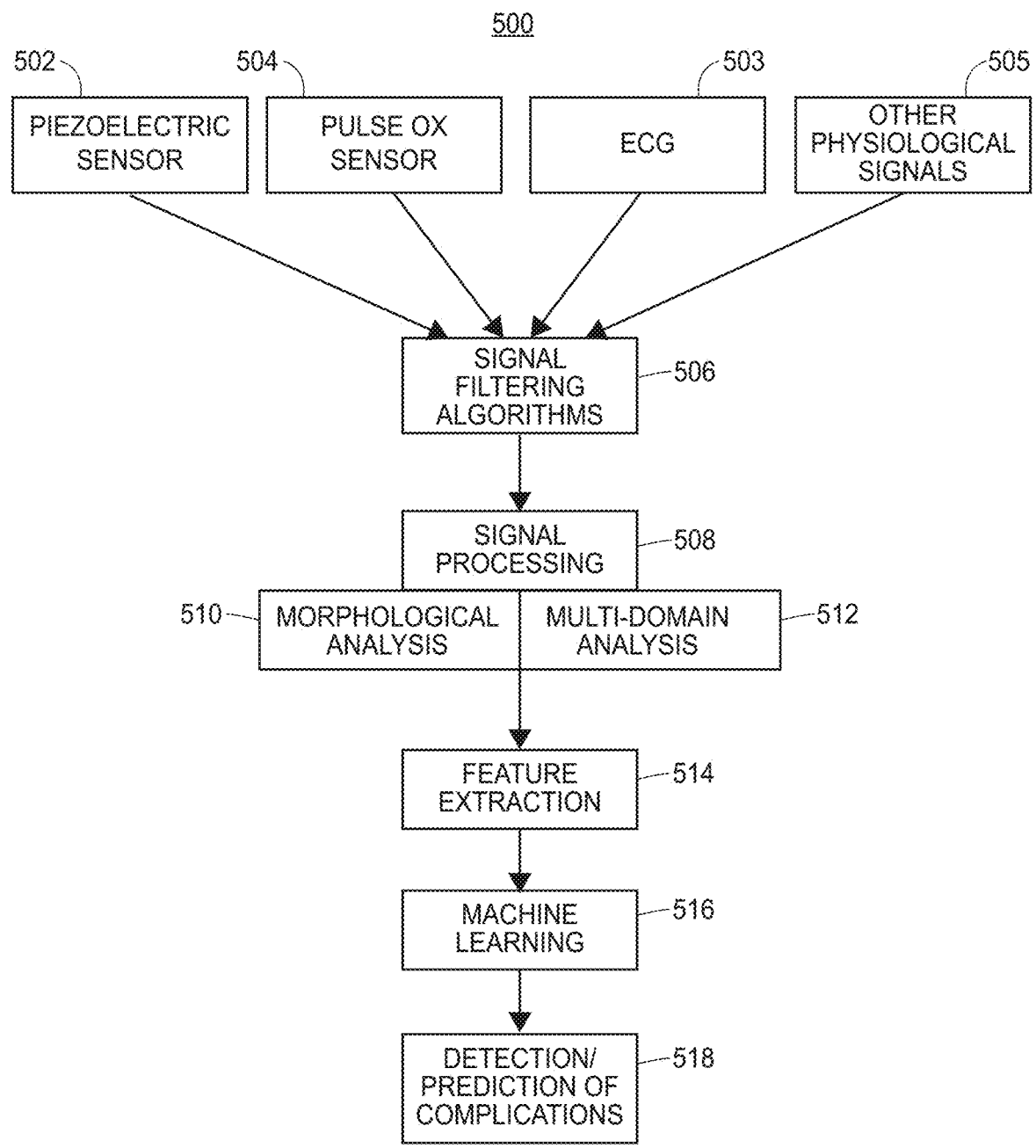
FIG. 6 is a flow diagram of operation of signal processor of FIG. 4, in accordance with another example implementation of FIG. 1.

The process 500 in FIG. 6 is similar to that of process 400, except that in addition to data collected from a piezoelectric sensor 502 and a pulse-oximetry sensor 504, electrocardiogram (ECG) data is collected at a block 503 and other physiological signals may be collected at a block 505. These other physiological signals include temperature, tissue impedance, galvanic skin response, and movement, among other physiological signals.

FIGS. 9, 10, 11, and 12 illustrate an example scenario in which data is gathered from a sensor assembly with both piezoelectric and pulse-oximetry sensors. Signals from both sensors may be received from the same sensor assembly (e.g., on a finger) while a patient performs several physiologic maneuvers such as deep breathing, Valsalva, or others. Note, although FIGS. 9, 10, 11, and 12 illustrate data from both piezoelectric and pulse-oximetry sensors, additional data may be obtained from sensor assemblies with additional sensors, such as ECG, impedance, temperature and other signals.

Figure 9:
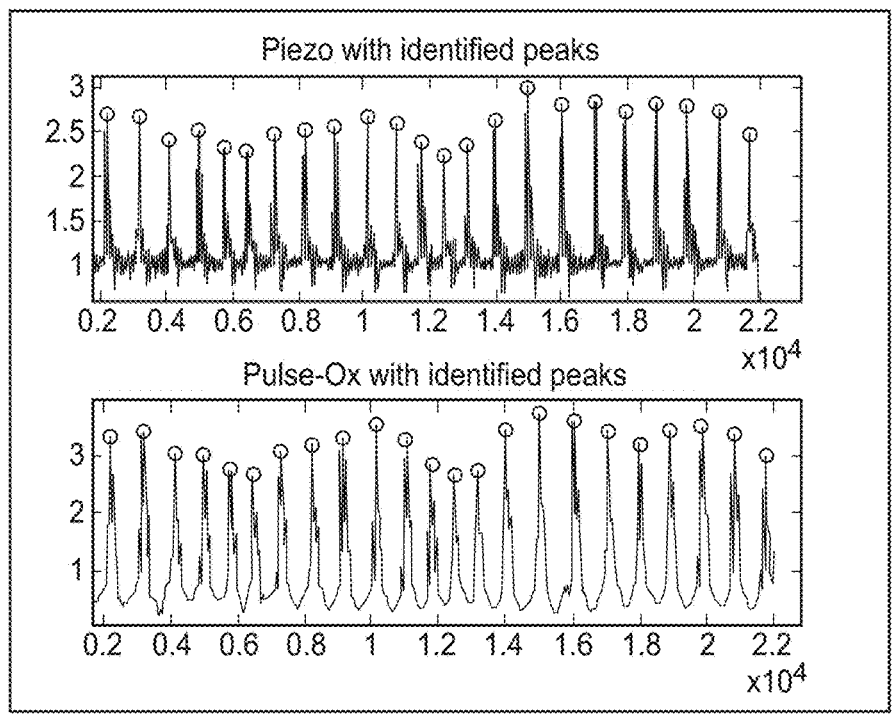
FIG. 9 illustrates an automated peak detection within a window of both piezoelectric and pulse-oximetry waveforms.

As illustrated in FIG. 9, an algorithm (e.g., executed by the signal-processing device 802) is capable of automatically detecting the peaks of each signal after denoising/filtering. FIG. 9 depicts an automated peak detection within a window of both piezoelectric and pulse-oximetry waveforms.

Figure 10:
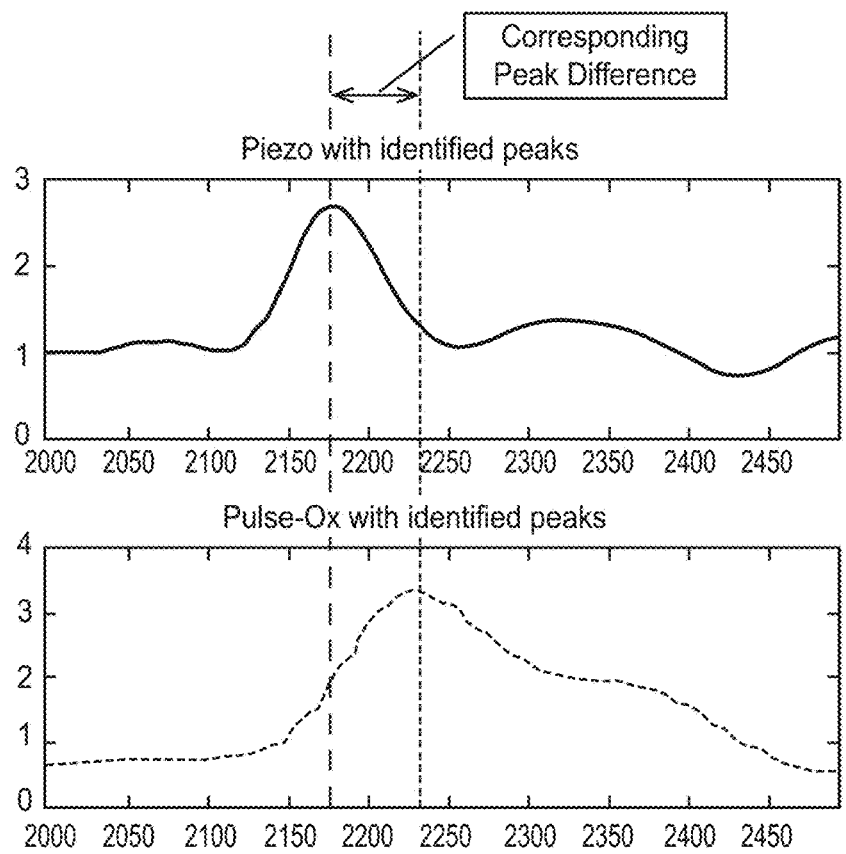
FIG. 10 illustrates example measured peak differences between corresponding peaks of the pulse-ox and piezoelectric waveforms.

Using the detected peaks, a distance in time ("x-axis") between peaks in the piezoelectric and peaks in the Pulse-ox is computed. FIG. 10 illustrates example measured peak differences between corresponding peaks of the pulse-ox and piezoelectric waveforms. In some implementations, in order to accurately measure the time difference between peaks in the two signals, a filtering and pre-processing of the two signals needs to be coordinated or conformed.

In the example scenario, both the piezoelectric and pulse-oximetry signals are collected from a patient while the subject performed some specified breathing exercises/maneuvers. The pulse-ox and the piezoelectric sensors may be disposed at a location very close to each other and on one the finger of the individual. The breathing maneuvers performed by the individual, whose data is depicted in FIGS. 9 and 10 may include, by way of example: (i) Baseline—sitting still and breathing normally; (ii) Valsava—closing one's mouth, pinching one's nose shut while pressing out as if blowing up a balloon; (iii) Deep breathing: repeated deep breaths; (iv) Fast breathing—repeated rapid breathing with shallow breaths; (v) BP cuff inflation and deflation—where a BP cuff is attached to the he subject's upper arm to which the other sensors are connected, the cuff is then inflated until the pulse-oximetry signal flat-lines, and, after keeping the cuff inflated for 2 minutes, the cuff is suddenly deflated to allow the return of normal circulation.

Figure 11:
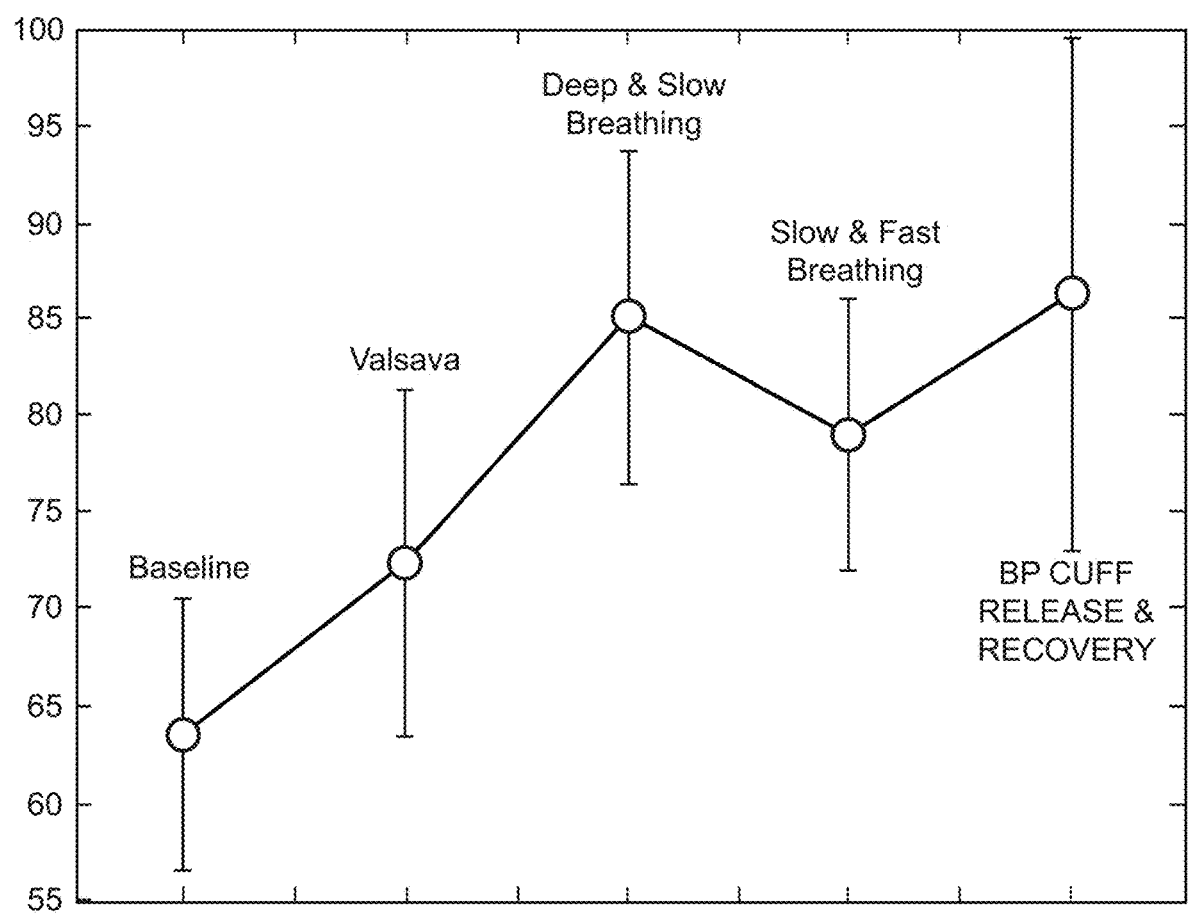
FIG. 11 depicts example means and standard deviations of different maneuvers calculated over corresponding peak differences between pulse-oximetry and piezoelectric waveforms.

FIG. 11 depicts the means and standard deviation of different maneuvers calculated over corresponding peak differences between pulse-oximetry and piezoelectric waveforms. It can clearly be seen that the peak-difference varies between baseline and other maneuvers.

Figure 12:
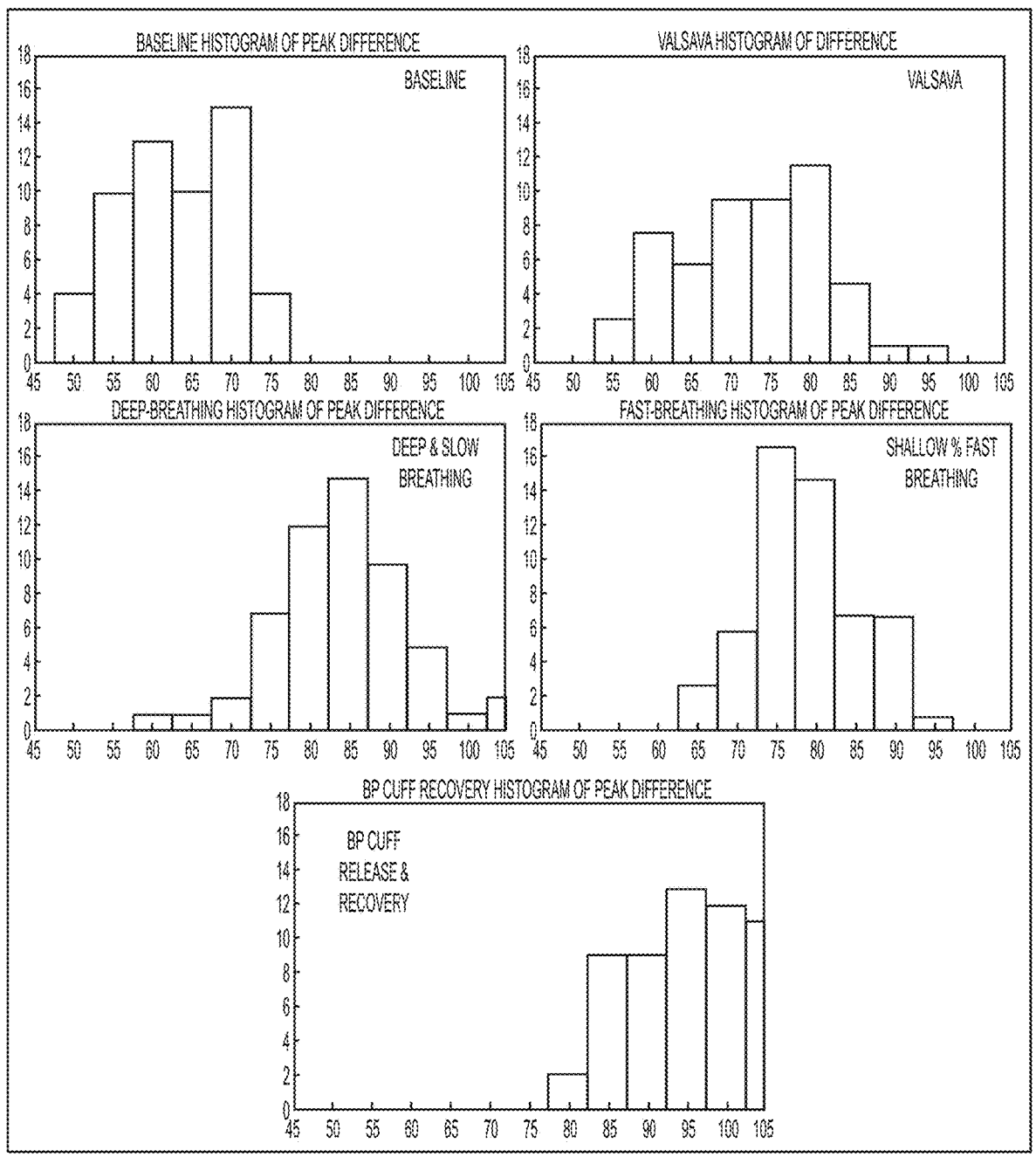
FIG. 12 includes example histograms of the peak differences between different maneuvers.

FIG. 12 includes example histograms of the peak differences between different maneuvers. Using fixed window sizes, the peak differences and corresponding distributions may be computed. As clearly seen in FIG. 12, the histograms vary considerably displaying the ability of computed peak difference to distinguish between different maneuvers.

FIGS. 13A-13G illustrate plots of piezoelectric sensor raw data compared to measured data from a pulse oximeter, under different conditions of a subject.

The output of the piezoelectric sensor may be linearly dependent on pressure, but the linear coefficient may vary based on location of a sensor assembly and tightness of fit. As such, physiological details may be inferred from relative height of features in the output signal and variation in the signal over time, not by absolute voltage output.

Figure 13A:
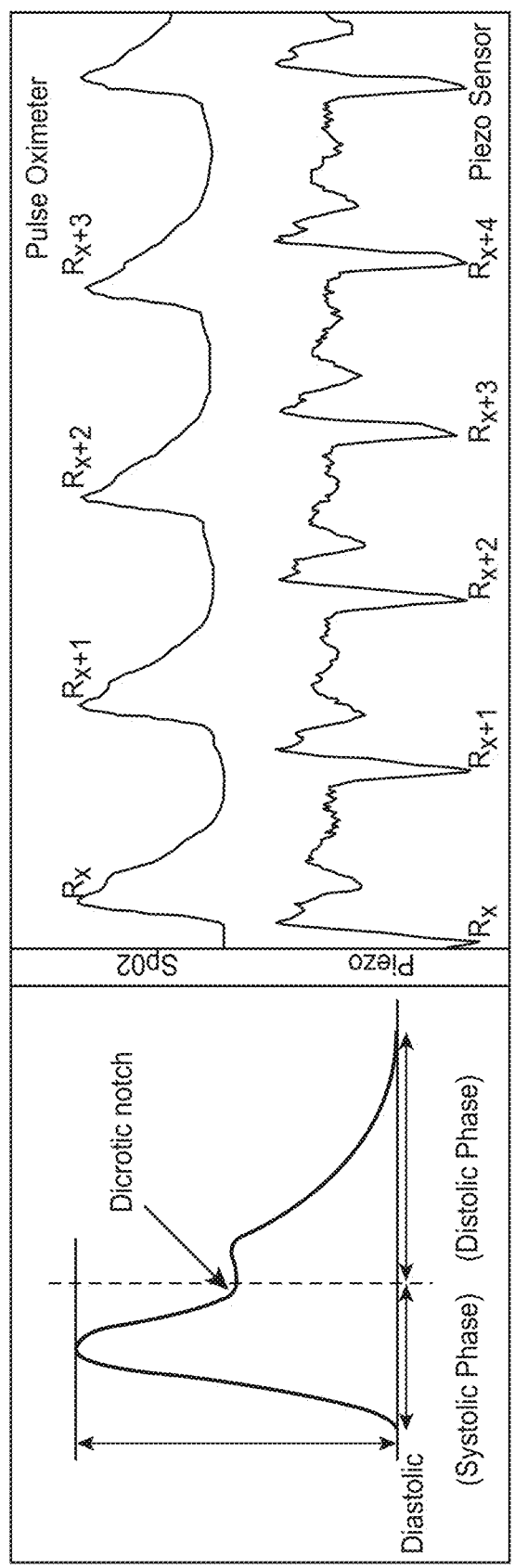
Figure 13B:
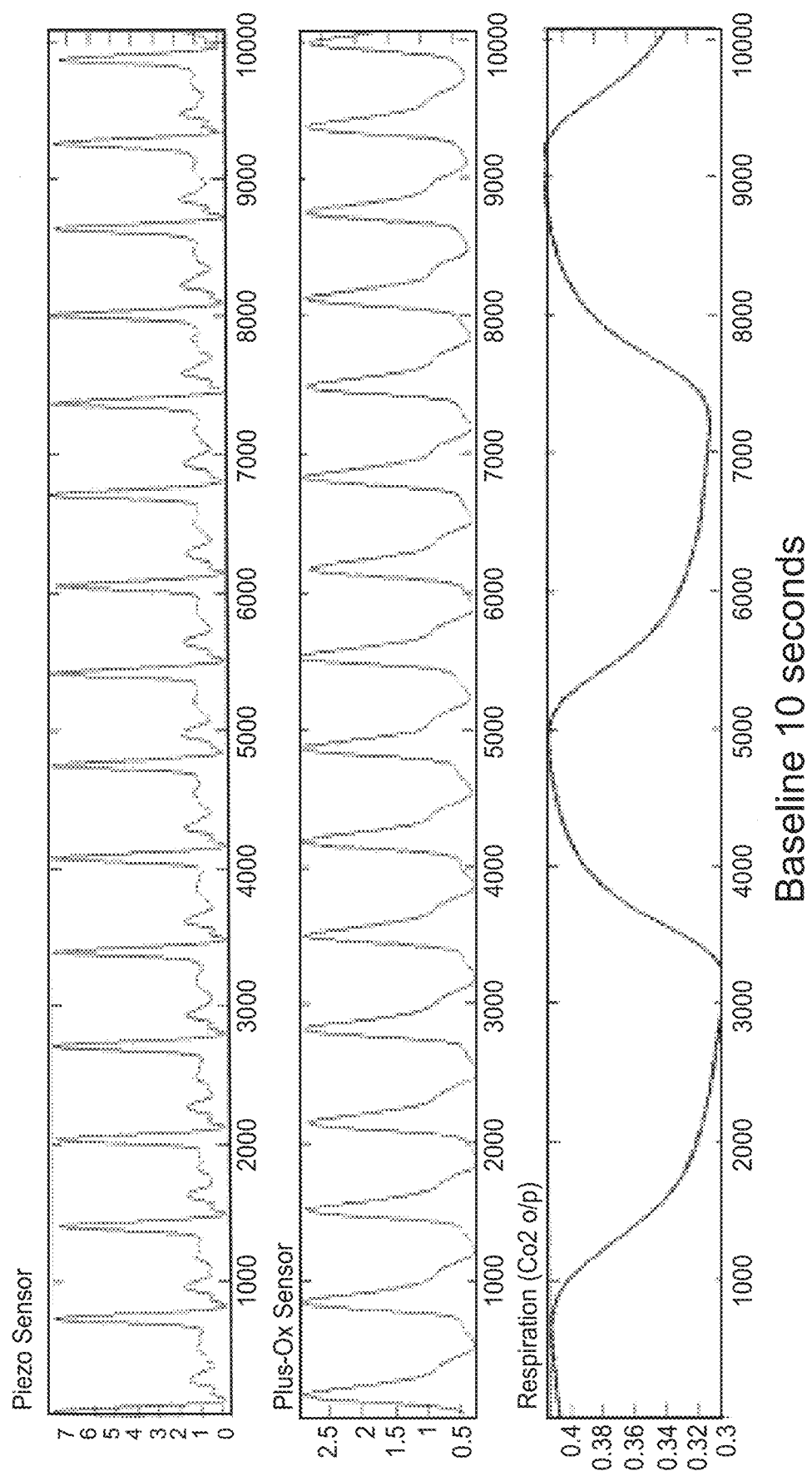
Figure 13C:
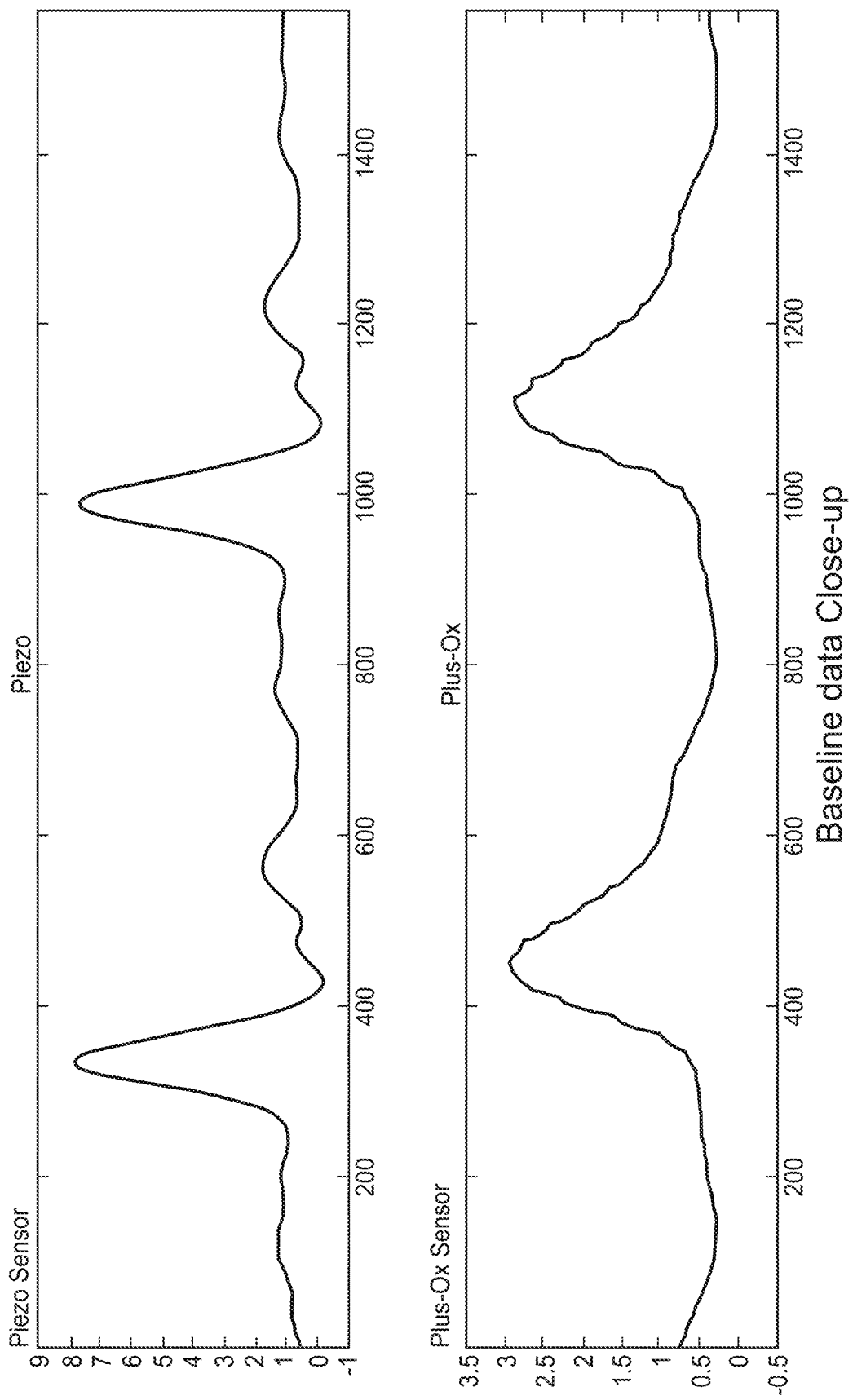
Figure 13D:
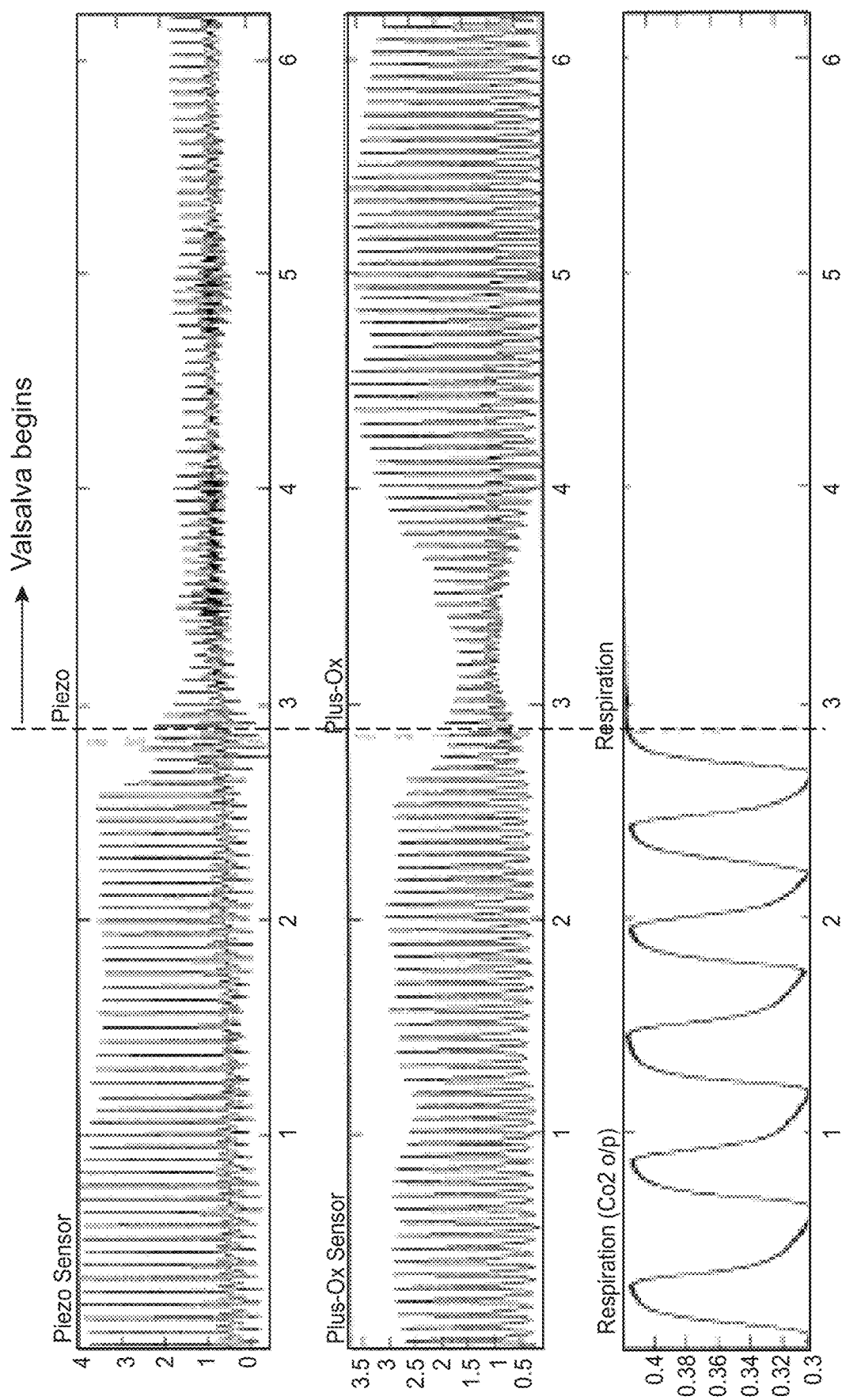
Figure 13F:
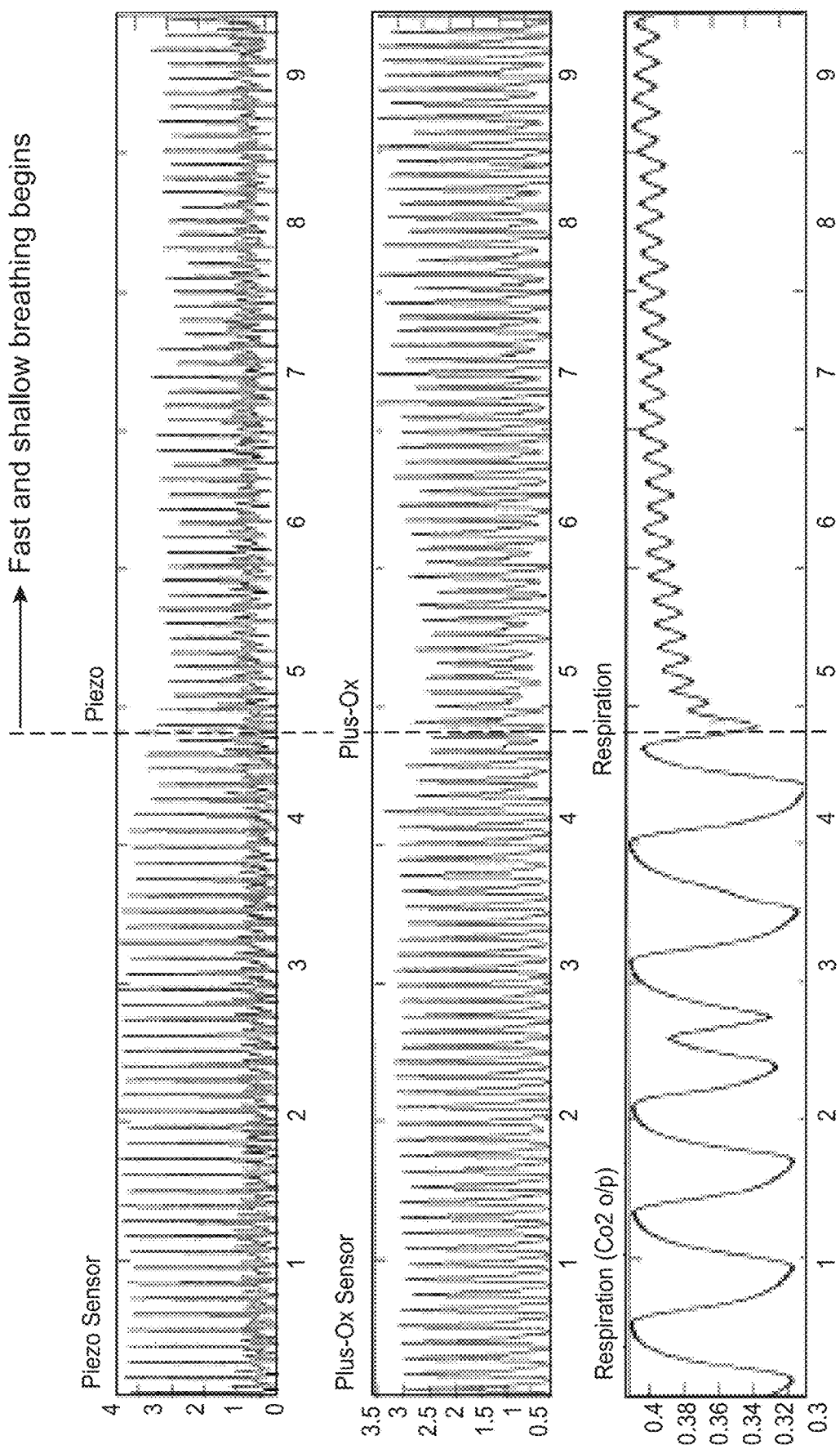
Figure 13G:
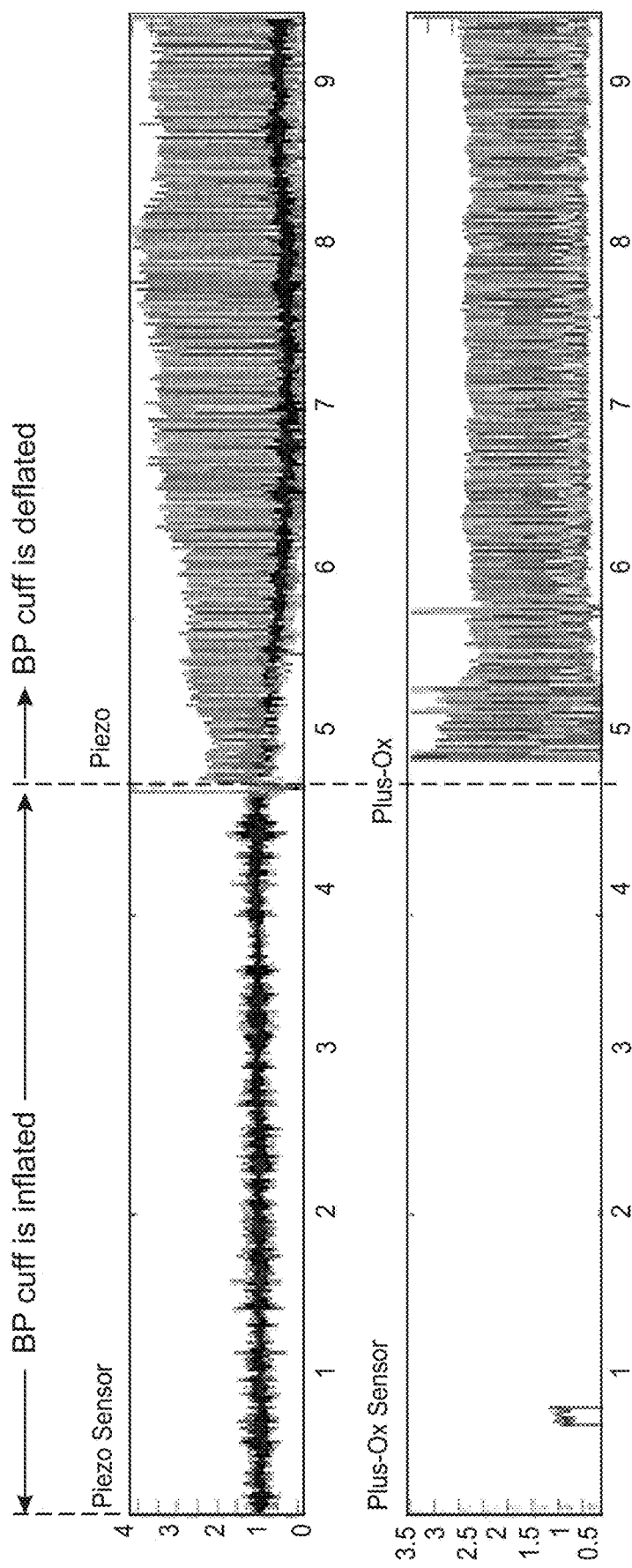

In some cases, the actual mechanical properties of the movement of the arterial wall (or vascular wall movements) may be measured producing rich waveform information similar to that produced by an indwelling catheter in the artery measuring pressure changes (see FIG. 13A) with some features actually being enhanced over traditional fluid column pressure monitoring. As shown in FIGS. 13A, 13B, and 13C, the waveform acquired from the piezoelectric sensor is very similar but also richer in features than the waveform produced by the pulse-oximetry sensor. Also, as shown in FIGS. 13D, 13E, 13F, and 13G the piezoelectric waveform may include unique trends which can be utilized to distinguish between different breathing maneuvers including Valsalva (see FIG. 13D), deep breathing (see FIG. 13E), fast breathing (see FIG. 13F), and BP cuff inflation (see FIG. 13G).

Further, high fidelity signals from piezoelectric sensors may be used, in some implementations, to reduce false alarms from traditional invasive and noninvasive monitoring methods for a number of applications. Such a use may reduce alarms caused by: (i) traditional pulse-oximetry in which the plethsymographic waveform produced is not of good fidelity due to motion or misapplication of the probe(s) or electrodes; (ii) dampening of arterial blood pressure monitoring waveforms from air bubbles and other problems caused by the nature of transducing pressures via fluid columns; and (iii) ECG alarming from the presence of electrical interference, motion induced artifacts of the ECG, or impedance respiratory signals or monitoring.

The nature of the direct mechanical high fidelity waveform, or raw signal data, produced by the piezoelectric sensor thus has the capability of acting as a signal "check" against electrical, water column transduction, and other signal acquisition methods. For example, maintenance of a clear piezoelectric waveform in the presence of a dampened invasive arterial pressure or pulse-oximetry waveform may indicate or produce a signal that would indicate that an alarm is due to faulty placement or function of sensors. Signals from the current piezoelectric sensor could also indicate that ectopy is true ectopy and not caused from motion or electrical interference, or the Signals from the current piezoelectric sensor could be used to confirm changes in respiratory rate.

Figure 14A:
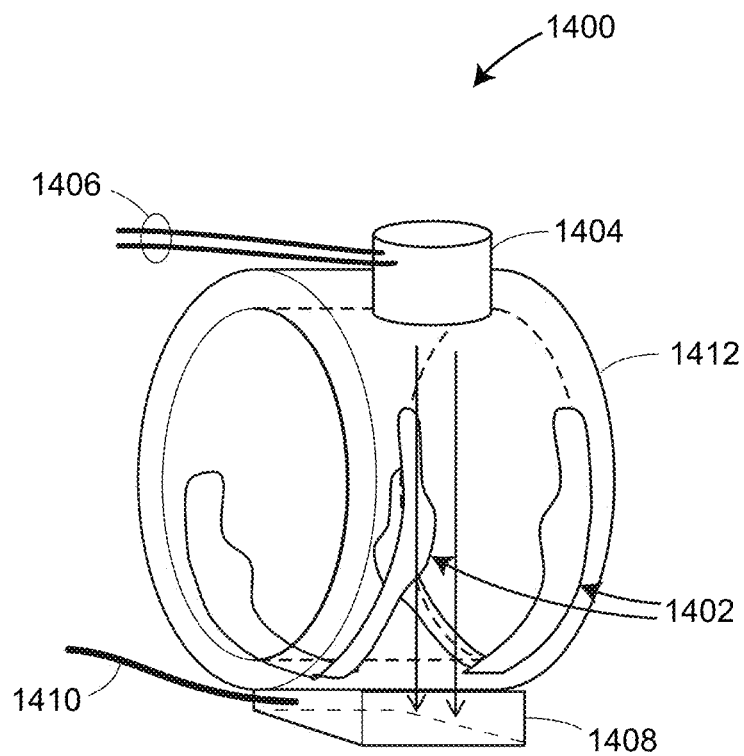
FIGS. 14A and 14B illustrate an example two sensor device, in the form of a piezoelectric sensor and pulse-oximetry sensor.
Figure 14B:
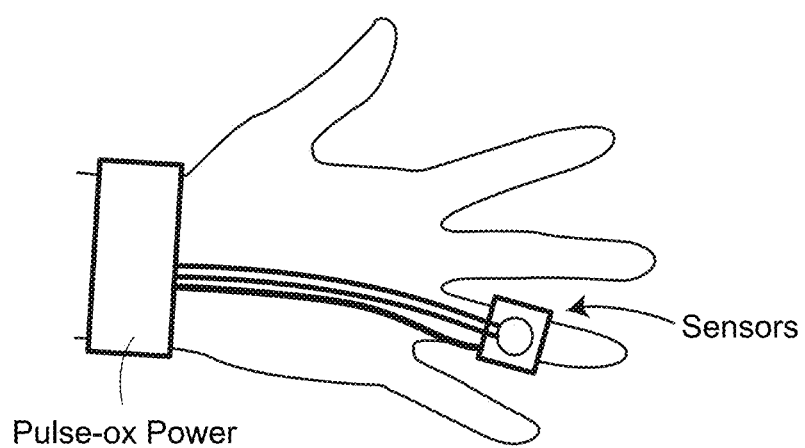

FIGS. 14A and 14B illustrates an example two sensor device 1400, or sensor assembly. The two sensor device 1400 includes one or more piezoelectric sensors 1402 and one or more other components associated with a pulse-oximetry sensor. The example pulse-oximetry sensor components may include a light source 1404 (powered via electrical connections 1406) and a light sensor 1408 operatively connected to one or more receiver connections 1410.

A support structure component 1412, such as a structure or band constructed as a polymer laminate, may support the piezoelectric sensors 1402 and the pulse-oximetry sensor components 1404 and 1408 such that they are positioned to gather vascular wall motion and blood flow dependent measurements. For example, as illustrated in FIG. 14B, the two device sensor 1400 may attach to a finger of a patient (e.g., via snap closures, buttons, buckles, or other attachments as discussed above). However, generally speaking, the support structure component 1412 and integrated attachment mechanisms (not shown) may allow the two sensor device to be attached to and gather measurements from any suitable portion of a patient's body. Also, although a pulse-oximetry sensor is illustrated with respect to FIG. 14, the two sensor device 1400 may include the piezoelectric sensors 1402 and a temperature sensor, motion sensor, actigraphy sensor, galvanic skin response sensor, impedance sensor, or any combination thereof.

In some implementations, the piezoelectric sensors 1402 may operate as passive sensor, whereas the pulse-oximetry sensor components 1404 and 1408 may require a power source to operate. In such a case, the two sensor device 1400, or pulse-oximetry components of the two sensor device 1400, may be operatively connected to a wearable power supply 1416. For example, the wearable power supply 1416 may include any suitable portable power source, such as batteries, solar panels, etc. It is clear, however, that the power supply 1416 may be integrated into the two sensor device 1400 such that the two sensor device does not require external power connections or leads.

Figure 15:
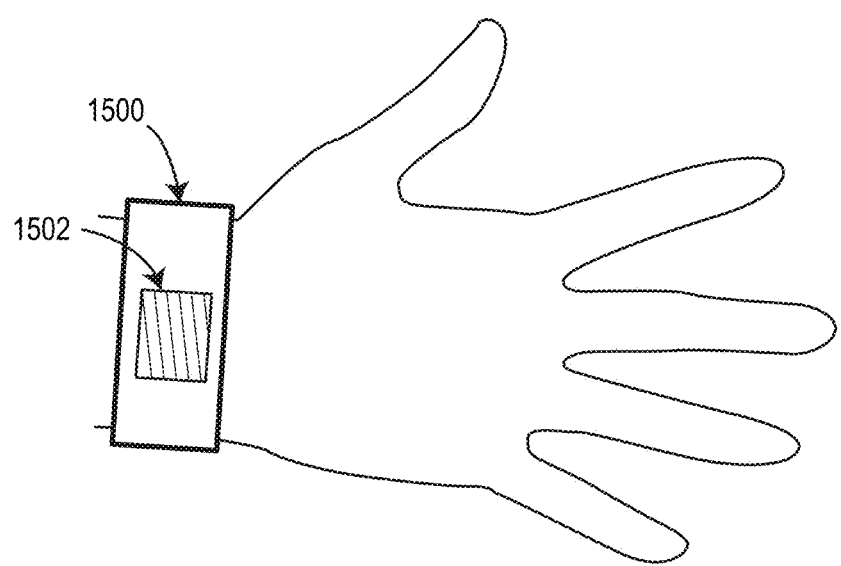
FIG. 15 illustrates an example wristband type device integrating a sensor assembly, such as the two sensor device illustrated in FIG. 14.

Further, although the two sensor device 1400 is illustrated as being attached to a patients finger as a "stand alone" device, a device substantially similar to that of the two sensor device 1400 may be integrated into another wearable device or article. For example, as illustrated in FIG. 15, an example two sensor device 1502 may be integrated into a wristband type device 1500. The wristband type device 1500 may be a smartwatch, activity tracking device, or other device, and may include one or more components separate from the two sensor device 1400. The wristband type device 1500 may also include one or more power sources (not shown) to power the two sensor device 1502 and one or more wired or wireless communication interfaces (e.g., WLAN, Bluetooth, radio frequency, etc.) to communicate gather data or derived signals from the two sensor device 1502. This same form factor may be used on the ankle or other locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. An apparatus comprising:
   a wearable sensor assembly including a flexible band having a polymer layer and a sensing layer both positioned for mounting the wearable sensor onto a sensing region of a subject for measuring vascular wall motion and blood flow dependent measurements over the sensing region, the wearable sensor comprising:
   (i) a piezoelectric sensor for measuring raw signal data, in real time, of vascular wall motion and blood flow dependent measurements, wherein the piezoelectric sensor comprises a piezoelectric electrode structure in the sensing layer for measuring the raw signal data in response to physical movement of the sensor region as detected by the piezoelectric sensor, and
   (ii) a secondary sensor for collecting and extracting photoplethysmograph derived blood flow data and photoplethysmograph derived waveform features; and a signal processor configured to
   receive the raw signal data from the piezoelectric sensor,
   filter the received raw signal data from the piezoelectric sensor,
   perform signal decomposition on the filtered raw signal data from the piezoelectric sensor,
   analyze the received raw signal data from the piezoelectric sensor to extract one or more waveform features from the received raw signal data,
   analyze the photoplethysmograph derived blood flow data and the photoplethysmograph derived waveform features from the secondary sensor; and
   compare the analyzed blood flow data and the waveform features to the extracted one or more waveform features from the piezoelectric sensor by:
      determining a first set of one or more local peaks and waveform features in the received raw signal data from the piezoelectric sensor;
      determining a second set of one or more local peaks and waveform features in the blood flow data from the secondary sensor; and
      determining a peak and waveform feature difference profile between the first set and the second set
   to extract indicators of circulating vascular volume and/or vascular tone to characterize and/or predict vascular health of the subject for clinical decision making.

2. The apparatus of claim 1, wherein the wearable sensor assembly further comprises a motion sensor device for measuring motion data of changes in motion of the wearable sensor in response to changes in the location or orientation of the sensing region and/or of the subject, wherein the wearable sensor transmits the motion data to the signal processor.

3. The apparatus of claim 2, wherein the signal processor is further configured to cancel noise in the raw signal data based on the motion data.

4. The apparatus of claim 2, wherein the motion sensor is a gyroscopic sensor or an accelerometer.

5. The apparatus of claim 1, a hard backing layer for mounting the wearable sensor against the sensing region, wherein wearable sensor is coextensive with the hard backing layer, the hard backing layer defines an inner sensing surface and an outer mounting surface.

6. The apparatus of claim 5, further comprising a communication interface mounted to the outer mounting surface of the hard backing layer, wherein the communication interface is either a wireless or a wired communication interface.

7. The apparatus of claim 5, further comprising a self-contained power source of the piezoelectric sensor and/or the photoplethysmography sensor mounted to the hard backing layer.

8. The apparatus of claim 1, wherein the extracted waveform features from the secondary sensor are expressive of one or more of physiological features selected from the group consisting of (BP), pulse pressure (PP), pulse pressure variability (PPV), heart rate (HR), heart rate variability and complexity (HRV), arterial wall stiffness (AWS), blood flow (BF), blood volume (BV), pulse transit time (PTT) and respiratory rate (RR) are used to create early warning physiologic indices reflective of changes in human health as well as indices used for clinical decision support to restore health.

9. The apparatus of claim 8, wherein extracted waveform features and indices are measured in response to applied physiological changes.

10. The apparatus of claim 9, wherein the applied physiological changes comprise temperature changes produced by external stimuli or pressure changes resulting from at least one of blood flow occlusions proximal to the wearable sensor assembly, Valsalva maneuvers, leg lift maneuvers, or change in breathing maneuvers.

11. The apparatus of claim 1, wherein the signal processor is further configured to:
receive, in real-time, the raw signal data from the piezoelectric sensor;
suppress motion artifacts from the received the raw signal data from the piezoelectric sensor based on data from one or more motion sensors in the sensor assembly;
extract at least one of time-based or transform-based features from the raw signal data; and
determine whether an externally-generated physiological or monitoring alarm is a true alarm or a false alarm.

12. The apparatus of claim 11, wherein the physiological alarm is generated by at least one of pulse oximetry, arterial blood pressure monitoring, respiration monitoring, or ECG monitoring.

13. The apparatus of claim 1, wherein the wearable sensor further comprises a temperature sensor, motion sensor, actigraphy sensor, galvanic skin response sensor, impedance sensor, or a combination thereof.

14. The apparatus of claim 1, wherein the piezoelectric sensor comprises a polymer outer layer sandwiching two piezoelectric electrodes to form the piezoelectric electrode structure in the sensing layer.

15. The apparatus of claim 1, wherein the one or more extracted waveform features from the piezoelectric sensor are expressive of one or more physiological features selected from the group consisting of blood pressure (BP), pulse pressure (PP), pulse pressure variability (PPV), heart rate (HR), heart rate variability and complexity (HRV), arterial wall stiffness (AWS), blood flow (BF), blood volume (BV), pulse transit time (PTT), and respiratory rate (RR) changes in the sensing region over a sample time frame.

16. The apparatus of claim 1, wherein the signal processor is external to the wearable sensor assembly.

17. A therapeutic delivery system for administering a therapeutic treatment to a subject, the delivery system comprising:
the apparatus of claim 1; and
an administration system comprising a therapeutic delivery vehicle in communication with a therapeutic treatment processor that controls delivery of the therapeutic treatment in response to received patient status data, the therapeutic treatment processor containing the signal processor and
(i) coupled to receive the raw signal data from the piezoelectric sensor, in a closed loop manner,
(ii) implemented to store the one or more extracted waveform features of the sensing region in the patient status data, and
(iii) implemented to determine instructions for administering the therapeutic treatment, in response to the stored one or more extracted waveform features.

18. A therapeutic delivery system for administering a therapeutic treatment to a subject, the delivery system comprising:
the apparatus of claim 1; and
an administration system comprising a therapeutic delivery vehicle in communication with a therapeutic treatment processor that controls delivery of the therapeutic treatment in response to received patient status data, the therapeutic treatment processor
(i) coupled to the signal processor to receive the one or more extracted waveform features of the sensing region,
(ii) implemented to store the one or more extracted waveform features of the sensing region in the patient status data, and
(iii) implemented to determine instructions for administering the therapeutic treatment in response to the stored one or more extracted waveform features.

19. The apparatus of claim 1, wherein the signal processor is further configured to:
receive, in real-time, the raw signal data from the piezoelectric sensor;
suppress motion artifacts from the received the raw signal data from the piezoelectric sensor based on data from one or more motion sensors in the sensor assembly;
extract at least one of time-based or transform-based features from the raw signal data; and
predict, based on an input of the at least one of the time-based or the transform-based features to a machine learning prediction model, one or more targeted physiologic events.

20. The apparatus of claim 1, wherein the wearable sensor assembly is integrated into a wristband device, the wristband device configured to monitor health and activity.

21. The apparatus of claim 1, wherein the wearable sensor assembly is integrated into a head-mounted device, the head-mounted device configurable to monitor health and activity.

22. The apparatus of claim 1, wherein the wearable sensor assembly is integrated into a device wearable by a patient on at least one of an arm, wrist, hand, finger, ankle, foot, toe, leg, head, neck, chest, or waist.

23. The apparatus of claim 1, wherein the signal processor is configured to:
generate (i) a health report and/or (ii) alarm condition of a morphology of the sensing region of a subject and correlated to either vascular volume, vascular tone, the one or more features, or a combination thereof.

24. The apparatus of claim 1, wherein the signal processor is configured to:
generate (i) a health report and/or (ii) alarm condition of a predicted morphology of the sensing region of a subject and correlated to either vascular volume, vascular tone, the one or more features, or a combination thereof.

* * * * *

UNITED STATES PATENT AND TRADEMARK OFFICE
CERTIFICATE OF CORRECTION

PATENT NO. : 10,610,113 B2  
APPLICATION NO. : 14/675062  
DATED : April 7, 2020  
INVENTOR(S) : Kayvan Najarian et al.

It is certified that error appears in the above-identified patent and that said Letters Patent is hereby corrected as shown below:

In the Claims

At Column 18, Line 49, "sensor; and" should be -- sensor, and --.

At Column 19, Line 26, "(BP)," should be -- blood pressure (BP), --.

At Column 20, Line 19, "processor and" should be -- processor --.

Signed and Sealed this
Eighth Day of September, 2020

Andrei Iancu
*Director of the United States Patent and Trademark Office*